(12) United States Patent
Jakobsen et al.

(10) Patent No.: US 7,569,664 B2
(45) Date of Patent: *Aug. 4, 2009

(54) SINGLE CHAIN RECOMBINANT T CELL RECEPTORS

(75) Inventors: Bent Karsten Jakobsen, Oxfordshire (GB); Meir Glick, Stoughton, MA (US)

(73) Assignee: Immunocore Limited, Oxon (GB)

( * ) Notice: Subject to any disclaimer, the term of this patent is extended or adjusted under 35 U.S.C. 154(b) by 437 days.

This patent is subject to a terminal disclaimer.

(21) Appl. No.: 10/530,035

(22) PCT Filed: Oct. 3, 2003

(86) PCT No.: PCT/GB03/04310

§ 371 (c)(1),
(2), (4) Date: Aug. 29, 2005

(87) PCT Pub. No.: WO2004/033685

PCT Pub. Date: Apr. 22, 2004

(65) Prior Publication Data

US 2006/0166875 A1    Jul. 27, 2006

Related U.S. Application Data

(60) Provisional application No. 60/475,784, filed on Jun. 5, 2003.

(30) Foreign Application Priority Data

Oct. 9, 2002 (GB) .................................... 0223399
Feb. 5, 2003 (GB) .................................... 0302604
Feb. 22, 2003 (GB) .................................... 0304064

(51) Int. Cl.
*C07K 14/00* (2006.01)
*C07K 17/00* (2006.01)

(52) U.S. Cl. ..................................... 530/350; 436/501

(58) Field of Classification Search ....................... None
See application file for complete search history.

(56) References Cited

FOREIGN PATENT DOCUMENTS

| WO | WO 96 18105 A | 6/1996 |
| WO | WO 99 18129 A | 4/1999 |
| WO | WO 99/60120 | * 11/1999 |
| WO | WO 00 31239 A | 6/2000 |

OTHER PUBLICATIONS

Chung et al. "Functional Three-Domain Single-Chain T-Cell Receptors"; Proceedings of the National Academy of Sciences of USA, National Academy of Science, Washington, US.; vol. 91, No. 26, Dec. 20, 1994, pp. 12654-12658, XP002039051.

* cited by examiner

*Primary Examiner*—G. R Ewoldt
*Assistant Examiner*—Amy E Juedes
(74) *Attorney, Agent, or Firm*—Banner & Witcoff, Ltd.

(57) ABSTRACT

A single chain T cell receptor (scTCR) comprising an α segment constituted by a TCR α chain variable region sequence fused to the N terminus of a TCR α chain constant region extracellular sequence, a β segment constituted by a TCR β chain variable region fused to the N terminus of a TCR β chain constant region extracellular sequence, and a linker sequence linking the C terminus of the α segment to the N terminus of the β segment, or vice versa, the constant region extracellular sequences of the α and β segments being linked by a disulfide bond, the length of the linker sequence and the position of the disulfide bond being such that the variable region sequences of the α and β segments are mutually orientated substantially as in native αβ T cell receptors. Complexes of two or more such scTCRs, and use of the scTCRs in therapy and in various screening applications are also disclosed.

27 Claims, 8 Drawing Sheets

Figure 1a atgcagaaggaagtggagcagaactctggacccctcagtgttccagagggagccatt
gcctctctcaactgcacttacagtgaccgaggttcccagtccttcttctggtacaga
caatattctgggaaaagccctgagttgataatgtccatatactccaatggtgacaaa
gaagatggaaggtttacagcacagctcaataaagccagccagtatgtttctctgctc
atcagagactcccagcccagtgattcagccacctacctctgtgccgttacaactgac
agctgggggaaattgcagtttggagcagggacccaggttgtggtcaccccagatatc
cagaaccctgaccctgccgtgtaccagctgagagactctaaatccagtgacaagtct
gtctgcctattcaccgattttgattctcaaacaaatgtgtcacaaagtaaggattct
gatgtgtatatcacagacaaatgtgtgctagacatgaggtctatggacttcaagagc
aacagtgctgtggcctggagcaacaaatctgactttgcatgtgcaaacgccttcaac
aacagcattattccagaagacaccttcttccccagcccagaaagttcctaa

Figure 1b atgaacgctggtgtcactcagaccccaaaattccaggtcctgaagacaggacagagc
atgacactgcagtgtgcccaggatatgaaccatgaatacatgtcctggtatcgacaa
gacccaggcatggggctgaggctgattcattactcagttggtgctggtatcactgac
caaggagaagtccccaatggctacaatgtctccagatcaaccacagaggatttcccg
ctcaggctgctgtcggctgctccctcccagacatctgtgtacttctgtgccagcagg
ccgggactagcgggagggcgaccagagcagtacttcgggccgggcaccaggctcacg
gtcacagaggacctgaaaaacgtgttccacccgaggtcgctgtgtttgagccatca
gaagcagagatctcccacacccaaaaggccacactggtgtgcctggccacaggcttc
taccccgaccacgtggagctgagctggtgggtgaatgggaaggaggtgcacagtggg
gtctgcacagaccgcagcccctcaaggagcagccgccctcaatgactccagatac
gctctgagcagccgcctgagggtctcggccaccttctggcaggaccccgcaaccac
ttccgctgtcaagtccagttctacgggctctcggagaatgacgagtggacccaggat
agggccaaacccgtcacccagatcgtcagcgccgaggcctggggtagagcagactaa

Figure 2a

MQ
K₁EVEQNSGPL SVPEGAIASL NCTYSDRGSQ SFFWYRQYSG KSPELIMSIY
SNGDKEDGRF TAQLNKASQY VSLLIRDSQP SDSATYLCAV TTDSWGKLQF
GAGTQVVVTP DIQNPDPAVY QLRDSKSSDK SVCLFTDFDS QTNVSQSKDS
DVYITDK<u>C</u>VL DMRSMDFKSN SAVAWSNKSD FACANAFNNS IIPEDTFFPS
PESS*

Figure 2b

M
N₁AGVTQTPKF QVLKTGQSMT LQCAQDMNHE YMSWYRQDPG MGLRLIHYSV
GAGITDQGEV PNGYNVSRST TEDFPLRLLS AAPSQTSVYF CASRPGLAGG
RPEQYFGPGT RLTVTEDLKN VFPPEVAVFE PSEAEISHTQ KATLVCLATG
FYPDHVELSW WVNGKEVHSG V<u>C</u>TDPQPLKE QPALNDSRYA LSSRLRVSAT
FWQDPRNHFR CQVQFYGLSE N<u>D</u>EWTQDRAK PVTQÍVSAEA WGRAD*

```
P   G   G   G   S   G   G   G   G   S   G   G   G   G
CCC GGG GGT GGC TCT GGC GGT GGC GGT TCA GGC GGT GGC GGA
GGG CCC CCA CCG AGA CCG CCA CCG CCA AGT CCG CCA CCG CCT

S   G   G   G   G   S   G   G   G   G   S   G   G   G
TCC GGC GGT GGC GGT TCG GGT GGC GGT GGC TCA GGC GGT GGC
AGG CCG CCA CCG CCA AGC CCA CCG CCA CCG AGT CCG CCA CCG

G   P
GGG CCC
CCC GGG
```

```
atgcagaaggaagtggagcagaactctggaccccctgagtgttccagagggagccattgcctctctcaactgcacttacagtgaccgaggttcccagtcctcttctggt
acagacaatattctgggaaagccctgagttgatatgtcctatcttccaagtgtacagcagcaagcttacaactgacacagccagcagtgt
ttctctgctcatcagagactcccagccctgaccctgccgtgattgagccactcctctgtgccttacaactgacgacagcagcagttcagtttgagcagggaccaggttgtg
gtcacccagatatccagaacctgatgtgtatatcacagacaaatgtgtgctagacatgaggtctaaagacaacagtgctgtgcctgagcaacaaatctga
tgtcaaagttctgatgtgtcaaacagcattattccagaagacacctctctcccaacgtgactcaagaacattcccccgggttgcctcggcgttcaggcgt
cttgcatgtgcaaacgcctcaacaacgcctcaacatgtgcggtggctcaggtcgcggtggctcaggtcgcggtggctcaggtcagggcgctccagtctccagggcgtg
tgacactgcagtgtgccagagcatagaactatacatgtcctgatcaacacagagatctctccagatcaacacagagattccgtctcaggctgtctggctgaccatcgt
tgaccaaggagagagagtcccccatagcggagctagcggaggcgagcagtactcttcgggcgcgggaccactgtgcctgcacactggggaggcctgcggagcagtcaggacctctgaggctgttgagctgaccgc
gccagcagcaggactagcaggaggcgagatctcccacagacccccaaaaggccacactggggaggctgcgacagagccccctcaaggagcagccccctaatgactctgcctgcaggtcctgaatacagctctgagcagcccctgagcagcccctggggctctggggtccggcagccg
tgtttgagccatcagaagcagagatcagtactaagaagcagtctctgcacagagtcctgccaggatctctgcacagaccccaaaaaggccacactggggaggctgcgacagagccccctcaaggagcagccccctaatgactctgcctgcaggtcctgaatacagctctgagcagcccctgagcagcccctggggctctggggtccggcagccg
gaagaggtgcacatggggaccccccgccaaccactccgctgtcaagtccagtcctgagatgaatgacgagtgaccagtggacccagtaggcaacccgtcaccagatcgtca
ttctgcaggaccgagcctgggtagagcagactaa
```

Figure 5b

```
MQKEVEQNSGPLSVPEGAIASLNCTYSDRGSQSFFWYRQYSGKSPELIMSIYSNGDKEDGR
FTAQLNKASQYVSLLIRDSQPSDSATYLCAVTTDSWGKLQFGAGTQVVVTPDIQNPDPAV
YQLRDSKSSDKSVCLFTDFDSQTNVSQSKDSDVYITDKCVLDMRSMDFKSNSAVAWSNKS
DFACANAFNNSIIPEDTFFPSPGGGSGGGGSGGGGSGGGGSGGGGSGGGGSGGGPNAGVT
QTPKFQVLKTGQSMTLQCAQDMNHEYMSWYRQDPGMGLRLIHYSVGAGITDQGEVPNG
YNVSRSTTEDFPLRLLSAAPSQTSVYFCASRPGLAGGRPEQYFGPGTRLTVTEDLKNVFPP
EVAVFEPSEAEISHTQKATLVCLATGFYPDHVELSWWVNGKEVHSGVCTDPQPLKEQAL
NDSRYALSSRLRVSATFWQDPRNHFRCQVQFYGLSENDEWTQDRAKPVTQIVSAEAWGR
A D Stop
```

SINGLE CHAIN RECOMBINANT T CELL RECEPTORS

This application is a U.S. National Stage application of co-pending PCT application PCT/GB2004/004310 filed Oct. 3, 2003, which claims the priority of Great Britain Patent Application No. 0223399.7, filed Oct. 9 2002; Great Britain Patent Application No. 0302604.4, filed Feb. 5, 2003; Great Britain Patent Application No. 0304064.9, filed Feb. 22, 2003; and U.S. Provisional Patent Application No. 60/475,784, filed Jun. 5, 2003. These applications are incorporated herein by reference in there entireties.

The present invention relates to single-chain T cell receptors (TCRs).

BACKGROUND TO THE INVENTION

Native TCRs

As is described in, for example, WO 99/60120 TCRs mediate the recognition of specific Major Histocompatibility Complex (MHC)-peptide complexes by T cells and, as such, are essential to the functioning of the cellular arm of the immune system.

Antibodies and TCRs are the only two types of molecules which recognise antigens in a specific manner, and thus the TCR is the only receptor for particular peptide antigens presented in MHC, the alien peptide often being the only sign of an abnormality within a cell. T cell recognition occurs when a T-cell and an antigen presenting cell (APC) are in direct physical contact, and is initiated by ligation of antigen-specific TCRs with pMHC complexes.

The native TCR is a heterodimeric cell surface protein of the immunoglobulin superfamily which is associated with invariant proteins of the CD3 complex involved in mediating signal transduction. TCRs exist in $\alpha\beta$ and $\gamma\delta$ forms, which are structurally similar but have quite distinct anatomical locations and probably functions. The MHC class I and class II ligands are also immunoglobulin superfamily proteins but are specialised for antigen presentation, with a highly polymorphic peptide binding site which enables them to present a diverse array of short peptide fragments at the APC cell surface.

Two further classes of proteins are known to be capable of functioning as TCR ligands. (1) CD1 antigens are MHC class I-related molecules whose genes are located on a different chromosome from the classical MHC class I and class II antigens. CD1 molecules are capable of presenting peptide and non-peptide (eg lipid, glycolipid) moieties to T cells in a manner analogous to conventional class I and class II-MHC-pep complexes. See, for example (Barclay et al, (1997) The Leucocyte Antigen Factsbook $2^{nd}$ Edition, Acadmeic Press) and (Bauer (1997) Eur J Immunol 27 (6) 1366-1373)) (2) Bacterial superantigens are soluble toxins which are capable of binding both class II MHC molecules and a subset of TCRs. (Fraser (1989) Nature 339 221-223) Many superantigens exhibit specificity for one or two Vbeta segments, whereas others exhibit more promiscuous binding. In any event, superantigens are capable of eliciting an enhanced immune response by virtue of their ability to stimulate subsets of T cells in a polyclonal fashion.

The extracellular portion of native heterodimeric $\alpha\beta$TCR consists of two polypeptides each of which has a membrane-proximal constant domain, and a membrane-distal variable domain (see FIG. 1). Each of the constant and variable domains includes an intra-chain disulfide bond. The variable domains contain the highly polymorphic loops analogous to the complementarity determining regions (CDRs) of antibodies. CDR3 of the TCR interacts with the peptide presented by MHC, and CDRs 1 and 2 interact with the peptide and the MHC. The diversity of TCR sequences is generated via somatic rearrangement of linked variable (V), diversity (D), joining (J), and constant genes. Functional $\alpha$ chain polypeptides are formed by rearranged V-J-C regions, whereas $\beta$ chains consist of V-D-J-C regions. The extracellular constant domain has a membrane proximal region and an immunoglobulin region. There is a single $\alpha$ chain constant domain, known as TRAC, and two different $\beta$ constant domains, known as TRBC1 and TRBC2 (IMGT nomenclature). There are four amino acid changes between these $\beta$ constant domains, three of which are within the domains used to produce the single-chain TCRs of the present invention. These changes are all within exon 1 of TRBC1 and TRBC2: $N_4K_5$->$K_4N_5$ and $F_{37}$->$Y$ (IMGT numbering, differences TRBC1->TRBC2), the final amino acid change between the two TCR $\beta$ chain constant regions being in exon 3 of TRBC1 and TRBC2: $V_1$->$E$. The extent of each of the TCR extracellular domains is somewhat variable. However, a person skilled in the art can readily determine the position of the domain boundaries using a reference such as The T Cell Receptor Facts Book, Lefranc & Lefranc, Publ. Academic Press 2001.

Single Chain TCRs

Single-chain TCRs (scTCRs) are artificial constructs consisting of a single amino acid strand, which like native heterodimeric TCRs bind to MHC-peptide complexes. Unfortunately, attempts to produce functional alpha/beta analogue scTCRs by simply linking the alpha and beta chains such that both are expressed in a single open reading frame have been unsuccessful, presumably because of the natural instability of the alpha-beta soluble domain pairing.

Accordingly, special techniques using various truncations of either or both of the alpha and beta chains have been necessary for the production of scTCRs. These formats appear to be applicable only to a very limited range of scTCR sequences. Soo Hoo et al (1992) PNAS. 89 (10): 4759-63 report the expression of a mouse TCR in single chain format from the 2C T cell clone using a truncated beta and alpha chain linked with a 25 amino acid linker and bacterial periplasmic expression (see also Schodin et al (1996) Mol. Immunol. 33 (9): 819-29). This design also forms the basis of the m6 single-chain TCR reported by Holler et al (2000) PNAS. 97 (10): 5387-92 which is derived from the 2C scTCR and binds to the same H2-Ld-restricted alloepitope. Shusta et al (2000) Nature Biotechnology 18: 754-759 report using single-chain 2 C TCR constructs in yeast display experiments, which produced mutated TCRs with, enhanced thermal stability and solubility, this report also demonstrated the ability of these displayed 2C TCRs to selectively bind cells expressing their cognate pMHC. Khandekar et al (1997) J. Biol. Chem. 272 (51): 32190-7 report a similar design for the murine D10 TCR, although this scTCR was fused to MBP and expressed in bacterial cytoplasm (see also Hare et al (1999) Nat. Struct. Biol. 6 (6): 574-81). Hilyard et al (1994) PNAS. 91 (19): 9057-61 report a human scTCR specific for influenza matrix protein-HLA-A2, using a V$\alpha$-linker-V$\beta$ design and expressed in bacterial periplasm.

Chung et al (1994) PNAS. 91 (26) 12654-8 report the production of a human scTCR using a V$\alpha$-linker-V$\beta$-C$\beta$ design and expression on the surface of a mammalian cell line. This report does not include any reference to peptide-HLA specific binding of the scTCR. Plaksin et al (1997) J. Immunol. 158 (5): 2218-27 report a similar V$\alpha$-linker-V$\beta$-C$\beta$ design for producing a murine scTCR specific for an HIV gp120-H-2D$^d$ epitope. This scTCR is expressed as bacterial inclusion bodies and refolded in vitro.

Therapeutic Use

There is a need for targeting moieties capable of localising to cells affected by disease processes. Such targeting moieties could be utilised either to directly block the 'miss-directed' action of the immune system responsible for auto-immune disease or as a means of delivering cytotoxic agents to cancerous cells.

Ideally, molecules suitable for these applications require a specific affinity for a cell marker directly involved in the relevant disease process. Antibodies have been used for this purpose.

Screening Use

A number of important cellular interactions and cell responses, including the TCR-mediated immune synapse, are controlled by contacts made between cell surface receptors and ligands presented on the surfaces of other cells. These types of specific molecular contacts are of crucial importance to the correct biochemical regulation in the human body and are therefore being studied intensely. In many cases, the objective of such studies is to devise a means of modulating cellular responses in order to prevent or combat disease.

Therefore, methods with which to identify compounds that bind with some degree of specificity to human receptor or ligand molecules are important as leads for the discovery and development of new disease therapeutics. In particular, compounds that interfere with certain receptor-ligand interactions have immediate potential as therapeutic agents or carriers.

Advances in combinatorial chemistry, enabling relatively easy and cost-efficient production of very large compound libraries, have increased the scope for compound testing enormously. Now the limitations of screening programmes most often reside in the nature of the assays that can be employed, the production of suitable receptor and ligand molecules and how well these assays can be adapted to high throughput screening methods.

BRIEF DESCRIPTION OF THE INVENTION

This invention makes available a new class of alpha/beta-analogue scTCRs which are characterised by the presence of a disulfide bond between residues of the single amino acid strand, that bond contributing to the stability of the pairing between alpha and beta regions of the molecule. Such TCRs are useful for screening or therapeutic purposes.

BRIEF DESCRIPTION OF THE DRAWINGS

FIGS. 1a and 1b show respectively the nucleic acid sequences of the α (SEQ ID NO:35) and β (SEQ ID NO:36) chains of a soluble A6 TCR, mutated so as to introduce a cysteine codon. The shading indicates the introduced cysteine codons.

FIG. 2a shows the A6 TCR α chain extracellular amino acid sequence (SEQ ID NO:37), including the $T_{48} \rightarrow C$ mutation (underlined) used to produce the novel disulphide inter-chain bond, and FIG. 2b shows the A6 TCR β chain extracellular amino acid sequence (SEQ ID NO:38), including the $S_{57} \rightarrow C$ mutation (underlined) used to produce the novel disulphide inter-chain bond.

FIG. 3 shows the DNA (SEQ ID NO:39) and amino acid (SEQ ID NO:34) sequences of the Gly/Ser linker (30 mer).

FIG. 5a shows the DNA sequence of the scDiS A6 TCR (SEQ ID NO:40).

FIG. 5b shows the amino acid sequence of the scDiS A6 TCR (SEQ ID NO:41).

DETAILED DESCRIPTION OF THE INVENTION

Figure 4:
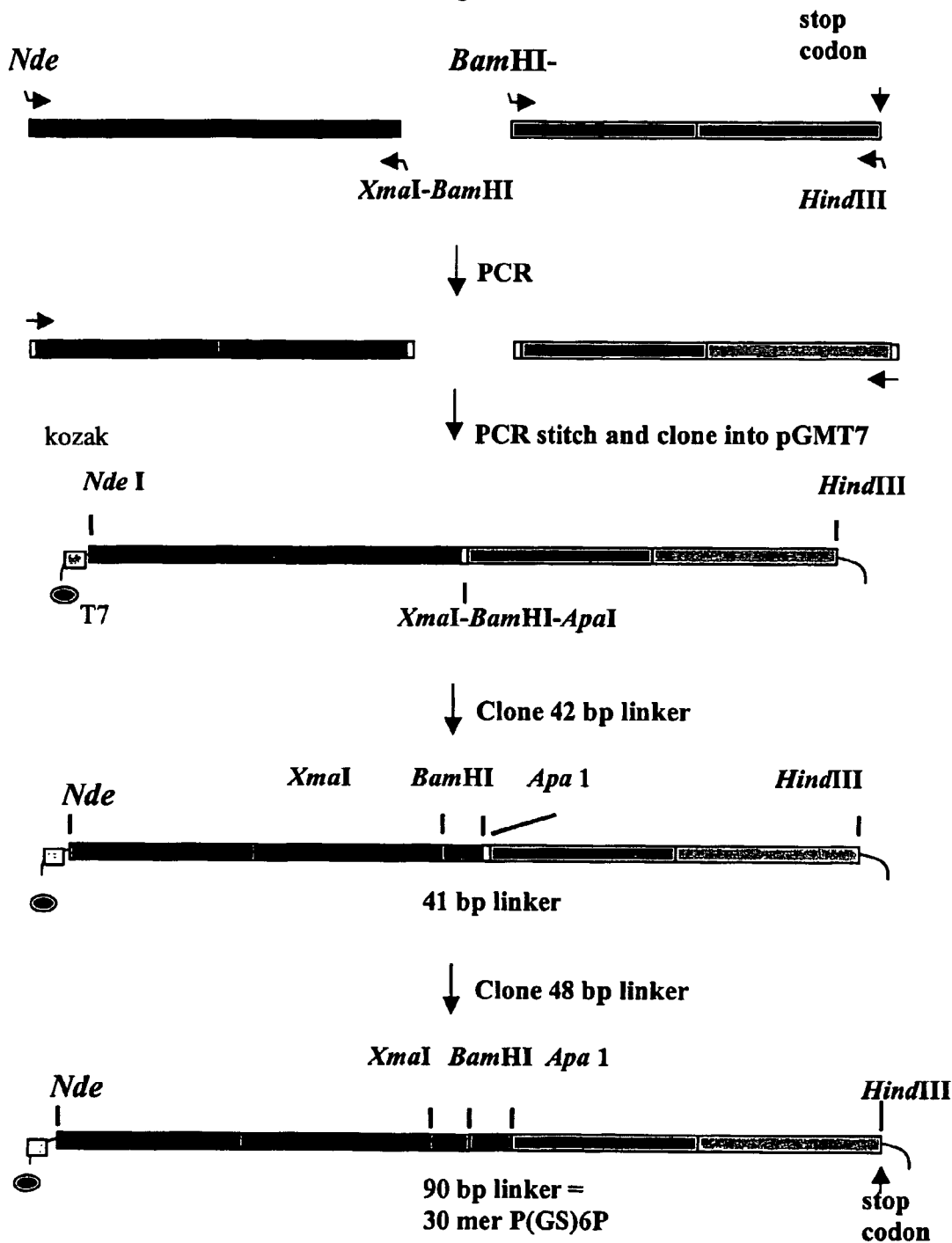
FIG. 4 summarizes the cloning strategy used to produce the scDiS A6 TCR.

The present invention provides a single chain T cell receptor (scTCR) comprising an α segment constituted by a TCR α chain variable region sequence fused to the N terminus of a TCR α chain constant region extracellular sequence, a β segment constituted by a TCR β chain variable region sequence fused to the N terminus of a TCR β chain constant region extracellular sequence, and a linker sequence linking the C terminus of the α segment to the N terminus of the β segment, or vice versa, the constant region extracellular sequences of the α and β segments being linked by a disulfide bond, the length of the linker sequence and the position of the disulfide bond being such that the variable region sequences of the α and β segments are mutually orientated substantially as in native αβ T cell receptors.

In the scTCR's of the invention the requirement that the variable region sequences of the α and β segments are mutually orientated substantially as in native αβ T cell receptors is tested by confirming that the molecule binds to the relevant TCR ligand (pMHC complex, CD1-antigen complex, superantigen or superantigen/pMHC complex)—if it binds, then the requirement is met. Interactions with pMHC complexes can be measured using a BIAcore 3000™ or BIAcore 2000™ instrument. Example 3 herein, or WO99/6120 respectively provide detailed descriptions of the methods required to analyse TCR binding to MHC-peptide complexes. These methods are equally applicable to the study of TCR/CD1 and TCR/superantigen interactions. In order to apply these methods to the study of TCR/CD1 interactions soluble forms of CD1 are required, the production of which are described in (Bauer (1997) Eur J Immunol 27 (6) 1366-1373).

α and β Segments

The constant region extracellular sequences present in the α and β segments preferably correspond to those of a human TCR, as do the variable region sequences present in the α and β segments. However, the correspondence between such sequences need not be 1:1 on an amino acid level. N- or C-truncation, and/or amino acid deletion and/or substitution relative to the corresponding human TCR sequences is acceptable, provided the overall result is mutual orientation of variable region sequences of the α and β segments as in native αβ T cell receptors and retention of peptide-MHC binding functionality. In particular, because the constant region extracellular sequences present in the α and β segments are not directly involved in contacts with the peptide-MHC complex to which the scTCR binds, they may be shorter than, or may contain substitutions or deletions relative to, extracellular constant domain sequences of native TCRs.

The constant region extracellular sequence present in the α segment may include a sequence corresponding to the extracellular constant Ig domain of a TCR α chain, and/or the constant region extracellular sequence present in the β segment may include a sequence corresponding to the extracellular constant Ig domain of a TCR β chain.

In one embodiment of the invention, the a segment corresponds to substantially all the variable region of a TCR α chain fused to the N terminus of substantially all the extracellular domain of the constant region of an TCR α chain; and/or the β segment corresponds to substantially all the variable region of a TCR β chain fused to the N terminus of substantially all the extracellular domain of the constant region of a TCR β chain.

In another embodiment, the constant region extracellular sequences present in the α and β segments correspond to the constant regions of the α and β chains of a native TCR truncated at their C termini such that the cysteine residues which form the native interchain disulfide bond of the TCR are excluded. Alternatively those cysteine residues may be substituted by another amino acid residue such as serine or alanine, so that the native disulfide bond is deleted. In addition, the native TCR β chain contains an unpaired cysteine residue and that residue may be deleted from, or replaced by a non-cysteine residue in, the β sequence of the scTCR of the invention.

In one particular embodiment of the invention, the TCR α and β chain variable region sequences present in the α and β segments may together correspond to the functional variable domain of a first TCR, and the TCR α and β chain constant region extracellular sequences present in the α and β segments may correspond to those of a second TCR, the first and second TCRs being from the same species. Thus the α and β chain variable region sequences present in the α and β segments may correspond to those of a first human TCR, and the α and β chain constant region extracellular sequences may correspond to those of a second human TCR. For example, A6 Tax sTCR constant region extracellular sequences can be used as framework onto which heterologous variable domains can be fused.

In another embodiment of the invention the TCR α and β chain variable region sequences present in the α and β segments together correspond to the functional variable domain of a first TCR, and the TCR α and β chain constant region extracellular sequences present in the α and β segments correspond to those of a second TCR, the first and second TCRs being from different species. In this embodiment it is preferred that the TCR α and β chain variable region sequences present in the α and β segments together correspond to the functional variable domain of a human TCR, and the TCR α and β chain constant region extracellular sequences present in the α and β segments correspond to those of a mouse TCR. Such embodiments of the present invention have the advantage that the scTCRs contain non-human constant region sequences which are likely to be immunogenic, and thus are likely to enhance the overall immune response to the dTCR when localised on its target cell. The immune response to aberrant cells such as cancer cells may thus be enhanced.

Linker

In the present invention, a linker sequence links the α and β segments, to form a single polypeptide strand. The linker sequence may, for example, have the formula -P-AA-P- wherein P is proline and AA represents an amino acid sequence wherein the amino acids are glycine and serine.

For the scTCR to bind an MHC-peptide complex, the α and β segments must be paired so that the variable region sequences thereof are orientated for such binding. Hence the linker should have sufficient length to span the distance between the C terminus of the α segment and the N terminus of the β segment, or vice versa. On the other hand excessive linker length should preferably be avoided, in case the end of the linker at the N-terminal variable region sequence blocks or reduces bonding of the scTCR to the target peptide-MHC complex.

For example, in the case where the constant region extracellular sequences present in the α and β segments correspond to the constant regions of the α and β chains of a native TCR truncated at their C termini such that the cysteine residues which form the native interchain disulfide bond of the TCR are excluded, and the linker sequence links the C terminus of the α segment to the N terminus of the β segment, the linker may consist of from 26 to 41, for example 29, 30, 31 or 32 amino acids, and a particular linker has the formula -PGGG-(SGGGG)$_5$-P- wherein P is proline, G is glycine and S is serine.

Disulfide Bond

A principle characterising feature of the scTCRs of the present invention is the disulfide bond between the constant region extracellular sequences of the α and β segments. That bond may correspond to the native interchain disulfide bond present in native dimeric αβ TCRs, or may have no counterpart in native TCRs, being between cysteines specifically incorporated into the constant region extracellular sequences of the α and β segments. In some cases, both a native and a non-native disulfide bond may be desirable in the present scTCRs.

The position of the disulfide bond is subject to the requirement that the variable region sequences of the α and β segments are mutually orientated substantially as in native αβ T cell receptors.

The disulfide bond may be formed by mutating non-cysteine residues on α and β segments to cysteine, and causing the bond to be formed between the mutated residues. Residues whose respective β carbons are approximately 6 Å (0.6 nm) or less, and preferably in the range 3.5 Å (0.35 nm) to 5.9 Å (0.59 nm) apart in the native TCR are preferred, such that a disulfide bond can be formed between cysteine residues introduced in place of the native residues. It is preferred if the disulfide bond is between residues in the constant immunoglobulin region, although it could be between residues of the membrane proximal region. Preferred sites where cysteines can be introduced to form the disulfide bond are the following residues in exon 1 of TRAC*01 for the TCR α chain and TRBC1*01 or TRBC2*01 for the TCR β chain:

| TCR α chain | TCR β chain | Native β carbon separation (nm) |
|---|---|---|
| Thr 48 | Ser 57 | 0.473 |
| Thr 45 | Ser 77 | 0.533 |

-continued

| TCR α chain | TCR β chain | Native β carbon separation (nm) |
|---|---|---|
| Tyr 10 | Ser 17 | 0.359 |
| Thr 45 | Asp 59 | 0.560 |
| Ser 15 | Glu 15 | 0.59 |

Now that the residues in human TCRs which can be mutated into cysteine residues to form a new interchain disulfide bond in scTCRs according to the invention have been identified, those of skill in the art will be able to mutate TCRs of other species in the same way to produce a scTCR of that species. In humans, the skilled person merely needs to look for the following motifs in the respective TCR chains to identify the residue to be mutated (the shaded residue is the residue for mutation to a cysteine).

```
α Chain Thr 48:  DSDVYITDKTVLDMRSMDFK
                 (amino acids 39-58 of exon 1 of
                 the TRAC*01 gene; SEQ ID NO:2)
α Chain Thr 45:  QSKDSDVYITDKTVLDMRSM
                 (amino acids 36-55 of exon 1 of
                 the TRAC*01 gene; SEQ ID NO:3)
α Chain Tyr 10:  DIQNPDPAVYQLRDSKSSDK
                 (amino acids 1-20 of exon 1 of
                 the TRAC*01 gene; SEQ ID NO:4)
α Chain Ser 15:  DPAVYQLRDSKSSDKSVCLF
                 (amino acids 6-25 of exon 1 of
                 the TRAC*01 gene; SEQ ID NO:5)
β Chain Ser 57:  NGKEVHSGVSTDPQPLKEQP
                 (amino acids 48-67 of exon 1 of
                 the TRBC1*01 & TRBC2*01 genes;
                 SEQ ID NO:6)
β Chain Ser 77:  ALNDSRYALSSRLRVSATFW
                 (amino acids 68-87 of exon 1 of
                 the TRBC1*01 & TRBC2*01 genes;
                 SEQ ID NO:7)
β Chain Ser 17:  PPEVAVFEPSEAEISHTQKA
                 (amino acids 8-27 of exon 1 of the
                 TRBC1*01 & TRBC2*01 genes;
                 SEQ ID NO:8)
β Chain Asp 59:  KEVHSGVSTDPQPLKEQPAL
                 (amino acids 50-69 of exon 1 of
                 the TRBC1*01 & TRBC2*01 genes gene;
                 SEQ ID NO:9)
β Chain Glu 15:  VFPPEVAVFEPSEAEISHTQ
                 (amino acids 6-25 of exon 1 of the
                 TRBC1*01 & TRBC2*01 genes;
                 SEQ ID NO:10)
```

In other species, the TCR chains may not have a region which has 100% identity to the above motifs. However, those of skill in the art will be able to use the above motifs to identify the equivalent part of the TCR α or β chain and hence the residue to be mutated to cysteine. Alignment techniques may be used in this respect. For example, Clustal W, available on the European Bioinformatics Institute website can be used to compare the motifs above to a particular TCR chain sequence in order to locate the relevant part of the TCR sequence for mutation.

The present invention includes within its scope αβ-analogue scTCRs, as well as those of other mammals, including, but not limited to, mouse, rat, pig, goat and sheep. Also included are human/non-human chimeric scTCRs as discussed above. As mentioned above, those of skill in the art will be able to determine sites equivalent to the above-described human sites at which cysteine residues can be introduced to form an inter-chain disulfide bond. For example, the following shows the amino acid sequences of the mouse Cα and Cβ soluble domains, together with motifs showing the murine residues equivalent to the human residues mentioned above that can be mutated to cysteines to form a TCR interchain disulfide bond (where the relevant residues are shaded):

Mouse Cα soluble domain:
PYIQNPEPAVYQLKDPRSQDSTLCLFTD-
  FDSQINVPKTMESGTFITDKTVLDMK AMDSKSN-
  GAIAWSNQTSFTCQDIFKETNATYPSSDVP (SEQ ID NO:11)

Mouse Cβ soluble domain:
EDLRNVTPPKVSLFEPS-
  KAELANKQKATLVCLARGFFPDHVELSW-
  WVNGREV HSGVSTDPQAYKESNYSYCLSSRLRV-
  SATFWHNPRNHFRCQVQFHGLSEEDK
  WPEGSPKPVTQNISAEAWGRAD (SEQ ID NO:12)

Murine equivalent of human α Chain Thr 48: ESGTFITDK-TVLDMKAMDSK (SEQ ID NO:13)

Murine equivalent of human α Chain Thr 45: KTMESGT-FITDKTVLDMKAM (SEQ ID NO:14)

Murine equivalent of human α Chain Tyr 10: YIQNPEP-AVYQLKDPRSQDS (SEQ ID NO:15)

Murine equivalent of human α Chain Ser 15: AVYQLKDPR-SQDSTLCLFTD (SEQ ID NO:16)

Murine equivalent of human β Chain Ser 57: NGREVHS-GVSTDPQAYKESN (SEQ ID NO:17)

Murine equivalent of human β Chain Ser 77: KESNYSY-CLSSRLRVSATFW (SEQ ID NO:18)

Murine equivalent of human β Chain Ser 17: PPKVSLFEPS-KAEIANKQKA (SEQ ID NO:19)

Murine equivalent of human β Chain Asp 59: REVHSGVST-DPQAYKESNYS (SEQ ID NO:20)

Murine equivalent of human β Chain Glu 15: VTPPKVS-LFEPSKAEIANKQ (SEQ ID NO:21)

As discussed above, the A6 Tax sTCR extracellular constant regions can be used as framework onto which heterologous variable domains can be fused. It is preferred that the heterologous variable region sequences are linked to the constant region sequences at any point between the disulfide bond and the N termini of the constant region sequences. In the case of the A6 Tax TCR α and β constant region sequences, the disulfide bond may be formed between cysteine residues introduced at amino acid residues 158 and 172 respectively. Therefore it is preferred if the heterologous α and β chain variable region sequence attachment points are between residues 159 or 173 and the N terminus of the α or β constant region sequences respectively.

Additional Aspects

A scTCR (which is preferably human) of the present invention may be provided in substantially pure form, or as a purified or isolated preparation. For example, it may be provided in a form which is substantially free of other proteins.

A plurality of scTCRs of the present invention may be provided in a multivalent complex. Thus, the present invention provides, in one aspect, a multivalent T cell receptor (TCR) complex, which comprises a plurality of soluble T cell receptors as described herein. Each of the plurality of soluble TCRs is preferably identical.

In the multivalent complex of the present invention, the scTCRs may be in the form of multimers, and/or may be present on or associated with a lipid bilayer, for example, a liposome.

In its simplest form, a multivalent scTCR complex according to the invention comprises a multimer of two or three or four or more T cell receptor molecules associated (e.g. covalently or otherwise linked) with one another, preferably via a linker molecule. Suitable linker molecules include, but are not limited to, multivalent attachment molecules such as avidin, streptavidin, neutravidin and extravidin, each of which has four binding sites for biotin. Thus, biotinylated TCR molecules can be formed into multimers of T cell receptors having a plurality of TCR binding sites. The number of TCR molecules in the multimer will depend upon the quantity of TCR in relation to the quantity of linker molecule used to make the multimers, and also on the presence or absence of any other biotinylated molecules. Preferred multimers are dimeric, trimeric or tetrameric TCR complexes.

Structures which are a good deal larger than TCR tetramers may be used in tracking or targeting cells expressing specific MHC-peptide complex. Preferably the structures are in the range 10 nm to 10 μm in diameter. Each structure may display multiple scTCR molecules at a sufficient distance apart to enable two or more TCR molecules on the structure to bind simultaneously to two or more MHC-peptide complexes on a cell and thus increase the avidity of the multimeric binding moiety for the cell.

Suitable structures for use in the invention, for forming complexes with one or a plurality of scTCRs, include membrane structures such as liposomes and solid structures which are preferably particles such as beads, for example latex beads. Other structures which may be externally coated with T cell receptor molecules are also suitable. Preferably, the structures are coated with T cell receptor multimers rather than with individual T cell receptor molecules.

In the case of liposomes, the T cell receptor molecules or multimers thereof may be attached to or otherwise associated with the membrane. Techniques for this are well known to those skilled in the art.

A label or another moiety, such as a toxic or therapeutic moiety, may be included in a multivalent scTCR complex of the present invention. For example, the label or other moiety may be included in a mixed molecule multimer. An example of such a multimeric molecule is a tetramer containing three scTCR molecules and one peroxidase molecule. This could be achieved by mixing the TCR and the enzyme at a molar ratio of 3:1 to generate tetrameric complexes, and isolating the desired complex from any complexes not containing the correct ratio of molecules. These mixed molecules could contain any combination of molecules, provided that steric hindrance does not compromise or does not significantly compromise the desired function of the molecules. The positioning of the binding sites on the streptavidin molecule is suitable for mixed tetramers since steric hindrance is not likely to occur.

In a further aspect, the invention provides a method for detecting MHC-peptide complexes, which comprises:
 a. providing a scTCR of the current invention
 b. contacting the scTCR with the MHC-peptide complexes; and detecting binding of the scTCR to the MHC-peptide complexes.

Therapeutic Use

The scTCR (or multivalent complex thereof) of the present invention may alternatively or additionally be associated with (e.g. covalently or otherwise linked to) a therapeutic agent which may be, for example, a toxic moiety for use in cell killing, or an immunostimulating agent such as an interleukin or a cytokine. A multivalent scTCR complex of the present invention may have enhanced binding capability for a TCR ligand such as a pMHC complex or CD1 molecule compared to a non-multimeric T cell receptor heterodimer. Thus, the multivalent scTCR complexes according to the invention are particularly useful for tracking or targeting cells presenting particular antigens in vitro or in vivo, and are also useful as intermediates for the production of further multivalent TCR complexes having such uses. The scTCR or multivalent scTCR complex may therefore be provided in a pharmaceutically acceptable formulation for use in vivo.

The invention also provides a method for delivering a therapeutic agent to a target cell, which method comprises contacting potential target cells with a scTCR or multivalent scTCR complex in accordance with the invention under conditions to allow attachment of the scTCR or multivalent scTCR complex to the target cell, said scTCR or multivalent scTCR complex being specific for the MHC-peptide complexes and having the therapeutic agent associated therewith.

In particular, the soluble scTCR or multivalent scTCR complex can be used to deliver therapeutic agents to the location of cells presenting a particular antigen. This would be useful in many situations and, in particular, against tumours. A therapeutic agent could be delivered such that it would exercise its effect locally but not only on the cell it binds to. Thus, one particular strategy envisages anti-tumour molecules linked to T cell receptors or multivalent scTCR complexes specific for tumour antigens.

Many therapeutic agents could be employed for this use, for instance radioactive compounds, enzymes (perforin for example) or chemotherapeutic agents (cis-platin for example). To ensure that toxic effects are exercised in the desired location the toxin could be inside a liposome linked to streptavidin so that the compound is released slowly. This will prevent damaging effects during the transport in the body and ensure that the toxin has maximum effect after binding of the scTCR to the relevant antigen presenting cells.

Other suitable therapeutic agents include:
 small molecule cytotoxic agents, i.e. compounds with the ability to kill mammalian cells having a molecular weight of less than 700 daltons. Such compounds could also contain toxic metals capable of having a cytotoxic effect. Furthermore, it is to be understood that these small molecule cytotoxic agents also include pro-drugs, i.e. compounds that decay or are converted under physiological conditions to release cytotoxic agents. Examples of such agents include cis-platin, maytansine derivatives, rachelmycin, calicheamicin, docetaxel, etoposide, gemcitabine, ifosfamide, irinotecan, melphalan, mitoxantrone, sorfimer sodiumphotofrin II, temozolmide, topotecan, trimetreate glucuronate, auristatin E vincristine and doxorubicin;
 peptide cytotoxins, i.e. proteins or fragments thereof with the ability to kill mammalian cells. Examples include ricin, diphtheria toxin, pseudomonas bacterial exotoxin A, DNAase and RNAase;
 radio-nuclides, i.e. unstable isotopes of elements which decay with the concurrent emission of one or more of α or β particles, or γ rays. Examples include iodine 131, rhenium 186, indium 111, yttrium 90, bismuth 210 and 213, actinium 225 and astatine 213;
 prodrugs, such as antibody directed enzyme pro-drugs;
 immuno-stimulants, i.e. moieties which stimulate immune response. Examples include cytokines such as IL-2, chemokines such as IL-8, platelet factor 4, melanoma growth stimulatory protein, etc, antibodies or fragments thereof, complement activators, xenogeneic protein domains, allogeneic protein domains, viral/bacterial protein domains and viral/bacterial peptides.

Soluble scTCRs or multivalent scTCR complexes of the invention may be linked to an enzyme capable of converting a prodrug to a drug. This allows the prodrug to be converted to the drug only at the site where it is required (i.e. targeted by the scTCR).

Examples of suitable MHC-peptide targets for the scTCR according to the invention include, but are not limited to, viral epitopes such as HTLV-1 epitopes (e.g. the Tax peptide restricted by HLA-A2; HTLV-1 is associated with leukaemia), HIV epitopes, EBV epitopes, CMV epitopes; melanoma epitopes (e.g. MAGE-1 HLA-A1 restricted epitope) and other cancer-specific epitopes (e.g. the renal cell carcinoma associated antigen G250 restricted by HLA-A2); and epitopes associated with autoimmune disorders, such as rheumatoid arthritis. Further disease-associated pMHC targets, suitable for use in the present invention, are listed in the HLA Factbook (Barclay (Ed) Academic Press), and many others are being identified.

Localising drug delivery through the specificity of scTCRs can potentially enhance a multitude of disease treatments.

Viral diseases for which drugs exist, e.g. HIV, SIV, EBV, CMV, would benefit from the drug being released or activated in the near vicinity of infected cells. For cancer, the localisation in the vicinity of tumours or metastasis would enhance the effect of toxins or immunostimulants. In autoimmune diseases, immunosuppressive drugs could be released slowly, having more local effect over a longer time-span while minimally affecting the overall immuno-capacity of the subject. In the prevention of graft rejection, the effect of immunosuppressive drugs could be optimised in the same way. For vaccine delivery, the vaccine antigen could be localised in the vicinity of antigen presenting cells, thus enhancing the efficacy of the antigen. The method can also be applied for imaging purposes.

The scTCRs of the present invention may be used to modulate T cell activation by binding to specific ligands such as pMHC and thereby inhibiting T cell activation. Autoimmune diseases involving T cell-mediated inflammation and/or tissue damage would be amenable to this approach, for example type I diabetes. Knowledge of the specific peptide epitope presented by the relevant pMHC is required for this use.

Medicaments in accordance with the invention will usually be supplied as part of a sterile, pharmaceutical composition which will normally include a pharmaceutically acceptable carrier. This pharmaceutical composition may be in any suitable form, (depending upon the desired method of administering it to a patient). It may be provided in unit dosage form, will generally be provided in a sealed container and may be provided as part of a kit. Such a kit would normally (although not necessarily) include instructions for use. It may include a plurality of said unit dosage forms.

The pharmaceutical composition may be adapted for administration by any appropriate route, for example by the oral (including buccal or sublingual), rectal, nasal, topical (including buccal, sublingual or transdermal), vaginal or parenteral (including subcutaneous, intramuscular, intravenous or intradermal) route. Such compositions may be prepared by any method known in the art of pharmacy, for example by admixing the active ingredient with the carrier(s) or excipient(s) under sterile conditions.

Screening Use

The scTCRs of the present invention are capable of utilisation in screening methods designed to identify modulators, including inhibitors, of the TCR-mediated cellular immune synapse.

As is know to those skilled in the art there are a number of assay formats that provide a suitable basis for protein-protein interaction screens of this type.

Amplified Luminescent Proximity Homogeneous Assay systems such as the AlphaScreen™, rely on the use of "Donor" and "Acceptor" beads that are coated with a layer of hydrogel to which receptor and ligand proteins can be attached. The interaction between these receptor and ligand molecules brings the beads into proximity. When these beads are subject to laser light a photosensitizer in the "Donor" bead converts ambient oxygen to a more excited singlet state. The singlet state oxygen molecules diffuse across to react with a chemiluminescer in the "Acceptor" bead that further activates fluorophores contained within the same bead. The fluorophores subsequently emit light at 520-620 nm, this signals that the receptor-ligand interaction has occurred. The presence of an inhibitor of the receptor-ligand interaction causes this signal to be diminished.

Surface Plasmon Resonance (SPR) is an interfacial optical assay, in which one binding partner (normally the receptor) is immobilised on a 'chip' (the sensor surface) and the binding of the other binding partner (normally the ligand), which is soluble and is caused to flow over the chip, is detected. The binding of the ligand results in an increase in concentration of protein near to the chip surface which causes a change in the refractive index in that region. The surface of the chip is comprised such that the change in refractive index may be detected by surface plasmon resonance, an optical phenomenon whereby light at a certain angle of incidence on a thin metal film produces a reflected beam of reduced intensity due to the resonant excitation of waves of oscillating surface charge density (surface plasmons). The resonance is very sensitive to changes in the refractive index on the far side of the metal film, and it is this signal which is used to detect binding between the immobilised and soluble proteins. Systems which allow convenient use of SPR detection of molecular interactions, and data analysis, are commercially available. Examples are the Iasys™ machines (Fisons) and the Biacore™ machines.

Other interfacial optical assays include total internal reflectance fluorescence (TIRF), resonant mirror (RM) and optical grating coupler sensor (GCS), and are discussed in more detail in Woodbury and Venton (*J. Chromatog. B*. 725 113-137 (1999)). The scintillation proximity assay (SPA) has been used to screen compound libraries for inhibitors of the low affinity interaction between CD28 and B7 ($K_d$ probably in the region of 4 µM (Van der Merwe et al *J. Exp. Med.* 185:393-403 (1997), Jenh et al, *Anal Biochem* 165(2) 287-93 (1998)). SPA is a radioactive assay making use of beta particle emission from certain radioactive isotopes which transfers energy to a scintillant immobilised on the indicator surface. The short range of the beta particles in solution ensures that scintillation only occurs when the beta particles are emitted in close proximity to the scintillant. When applied for the detection of protein-protein interactions, one interaction partner is labelled with the radioisotope, while the other is either bound to beads containing scintillant or coated on a surface together with scintillant. If the assay can be set up optimally, the radioisotope will be brought close enough to the scintillant for photon emission to be activated only when binding between the two proteins occurs.

A further aspect of the invention is a method of identifying an inhibitor of the interaction between an scTCR and a TCR ligand selected from MHC-peptide complexes, CD1-antigen complexes, superantigens and MHC-peptide/superantigen complexes comprising contacting the scTCR with a scTCR ligand binding partner, in the presence of and in the absence of a test compound, and determining whether the presence of the test compound reduces binding of the scTCR to the ligand, such reduction being taken as identifying an inhibitor.

A final aspect of the invention is a method of identifying a potential inhibitor of the interaction between an scTCR and TCR ligand selected from MHC-peptide complexes, CD1-antigen complexes, superantigens and MHC-peptide/superantigen complexes comprising contacting the scTCR or scTCR ligand binding partner with a test compound and determining whether the test compound binds to the scTCR and/or the ligand, such binding being taken as identifying a potential inhibitor. This aspect of the invention may find particular utility in interfacial optical assays such as those carried out using the BIAcore™ system.

Preferred features of each aspect of the invention are as for each of the other aspects mutatis mutandis. The prior art documents mentioned herein are incorporated to the fullest extent permitted by law.

EXAMPLES

The invention is further described in the following examples, which do not limit the scope of the invention in any way.

Example 1

Design of Primers and Mutagenesis of A6 Tax TCR α and β Chains to Introduce the Cysteine Residues Required for the Formation of a Novel Inter-chain Disulphide Bond For mutating A6 Tax threonine 48 of exon 1 in TRAC*01 to cysteine, the following primers were designed (mutation shown in lower case):

```
                                        (SEQ ID NO:22)
5'-C ACA GAC AAA tgT GTG CTA GAC AT (SEQ ID NO:23)
5'-AT GTC TAG GAG Aca TTT GTC TGT G
```

For mutating A6 Tax serine 57 of exon 1 in both TRBC1*01 and TRBC2*01 to cysteine, the following primers were designed (mutation shown in lower case):

```
                                        (SEQ ID NO:24)
5'-C AGT GGG GTC tGC ACA GAC CC (SEQ ID NO:25)
5'-GG GTC TGT GCa GAC CCC ACT G
```

PCR Mutagenesis:

Expression plasmids containing the genes for the A6 Tax TCR α or β chain were mutated using the α-chain primers or the β-chain primers respectively, as follows. 100 ng of plasmid was mixed with 5 µl 10 mM dNTP, 25 µl 10×Pfu-buffer (Stratagene), 10 units Pfu polymerase (Stratagene) and the final volume was adjusted to 240 µl with $H_2O$. 48 µl of this mix was supplemented with primers diluted to give a final concentration of 0.2 µM in 50 µl final reaction volume. After an initial denaturation step of 30 seconds at 95° C., the reaction mixture was subjected to 15 rounds of denaturation (95° C., 30 sec.), annealing (55° C., 60 sec.), and elongation (73° C., 8 min.) in a Hybaid PCR express PCR machine. The product was then digested for 5 hours at 37° C. with 10 units of DpnI restriction enzyme (New England Biolabs). 10 µl of the digested reaction was transformed into competent XL1-Blue bacteria and grown for 18 hours at 37° C. A single colony was picked and grown over night in 5 ml TYP+ampicillin (16 g/l Bacto-Tryptone, 16 g/l Yeast Extract, 5 g/l NaCl, 2.5 g/l $K_2HPO_4$, 100 mg/l Ampicillin). Plasmid DNA was purified on a Qiagen mini-prep column according to the manufacturer's instructions and the sequence was verified by automated sequencing at the sequencing facility of Department of Biochemistry, Oxford University. The respective mutated nucleic acid and amino acid sequences are shown in FIGS. 1a and 2a for the a chain and FIGS. 1b and 2b for the β chain.

Example 2

Design, Expression and Testing of a Single-chain A6 TCR Incorporating a Novel Disulphide Inter-chain Bond The expression vectors containing the DNA sequences of the mutated A6 TCR α and β chains incorporating the additional cysteine residues required for the formation of a novel disulphide prepared in Example 1 and as shown in FIGS. 1a and 1b were used as the basis for the production of a single-chain A6 TCR, with the exception that the stop codon (TAA) was removed from the end of the a chain sequence, as follows:

The scDiS A6 TCR contains a 30 amino acid linker sequence between the C-terminus of the TCR α chain and the N-terminus of the β chain. FIG. 3 shows the DNA and amino acid sequence of this linker. The cloning strategy employed to produce the scDiS A6 TCR is summarised in FIG. 4.

Briefly, the alpha and beta chains of the A6 dsTCR were amplified by PCR using primers containing restriction sites as shown in FIG. 4, i.e.:

```
Alpha 5' primer:                        (SEQ ID NO:26)
ccaaggccatatgcagaaggaagtggagcagaactct Alpha 3' primer:                        (SEQ ID NO:27)
ttgggcccgccggatccgcccccgggggaactttctgggctgggg Beta 5' primer:                         (SEQ ID NO:28)
tcccccgggggcggatccggcgggcccaacgctggtgtcactcag Beta 3' primer:                         (SEQ ID NO:29)
gggaagcttagtctgctctacccaggcctcg
```

The two fragments thus generated were PCR stitched using the 5' alpha and 3' beta primers to give a single-chain TCR with a short linker containing the sites XmaI-BamHI-ApaI. This fragment was cloned into pGMT7. The full length linker was then inserted in two stages, firstly a 42 bp fragment was inserted using the XmaI and BamHI sites:

```
                                        (SEQ ID NO:30)
5'-CC GGG GGT GGC TCT GGC GGT GGC GGT TCA GGC GGT
GGC G-3'

(SEQ ID NO:31)
3'-C CCA CCG AGA CCG CCA CCG CCA AGT CCG CCA CCG
CCT AG-5'
```

Secondly, a 48 bp fragment was inserted using the BamHI and ApaI sites to create a 90 bp linker between the 3' end of the alpha chain and the 5' end of the beta chain. The 48 bp fragment was made by PCR extension of a mixture of the following oligos:

```
                                        (SEQ ID NO:32)
5'- GC GGA TCC GGC GGT GGC GGT TCG GGT GGC GGT GGC
TC-3'

(SEQ ID NO:33)
3'- CCA AGC CCA CCG CCA CCG AGT CCG CCA CCG CCC
GGG TG -5'
```

The product of this extension was digested with BamHI and ApaI and ligated into the digested plasmid containing the 42 bp linker fragment.

The complete DNA and amino acid sequence of the scDiS A6 TCR is shown in FIGS. 5a and 5b respectively.

Expression and Purification of Single-chain Disulphide Linked A6 TCR:

The expression plasmid containing the single-chain disulphide linked A6 TCR was transformed into *E. coli* strain BL21pLysS, and single ampicillin-resistant colonies were grown at 37° C. in TYP (ampicillin 100 µg/ml) medium to $OD_{600}$ of 0.4 before inducing protein expression with 0.5 mM IPTG. Cells were harvested three hours post-induction by centrifugation for 30 minutes at 400 rpm in a Beckman J-6B. Cell pellets were re-suspended in a buffer containing 50 mM Tris-HCI, 25% (w/v) sucrose, 1 mM NaEDTA, 0.1% (w/v) NaAzide, 10 mM DTT, pH 8.0. After an overnight freeze-thaw step, re-suspended cells were sonicated in 1 minute bursts for a total of around 10 minutes in a Milsonix XL2020 sonicator using a standard 12 mm diameter probe. Inclusion body pellets were recovered by centrifugation for 30 minutes at 13000 rpm in a Beckman J2-21 centrifuge. Three detergent washes were then carried out to remove cell debris and membrane components. Each time the inclusion body pellet was homogenised in a Triton buffer (50 mM Tris-HCI, 0.5% Triton-X100, 200 mM NaCI, 10 mM NaEDTA, 0.1% (w/v) NaAzide, 2 mM DTT, pH 8.0) before being pelleted by centrifugation for 15 minutes at 13000 rpm in a Beckman J2-21. Detergent and salt was then removed by a similar wash in the following buffer: 50 mM Tris-HCl, 1 mM NaEDTA, 0.1% (w/v) NaAzide, 2 mM DTT, pH 8.0. Finally, the inclusion bodies were divided into 30 mg aliquots and frozen at −70° C. Inclusion body protein yield was quantitated by solubilising with 6M guanidine-HCl and measurement with a Bradford dye-binding assay (PerBio).

Figure 6:
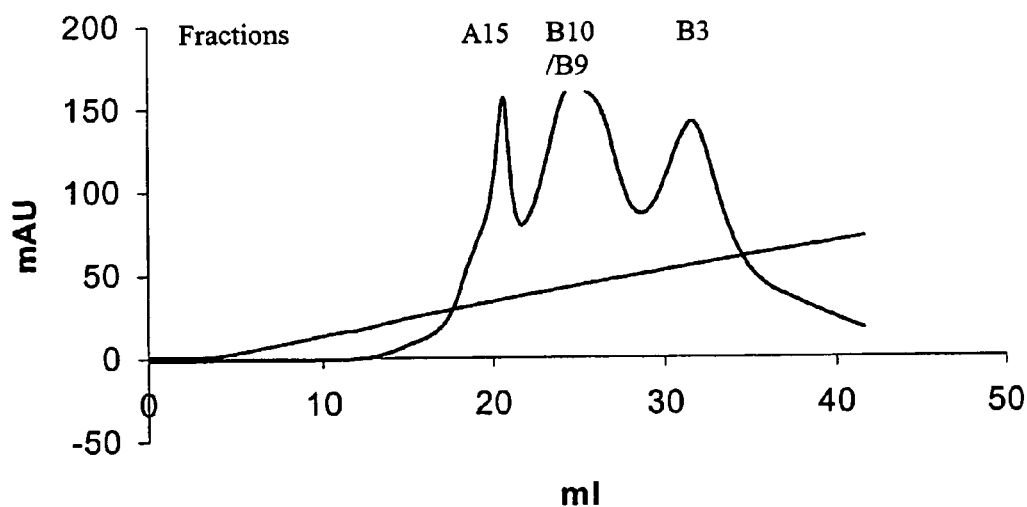
FIG. 6 illustrates the elution of the scDiS A6 TCR protein from a POROS 50HQ ion exchange column using a 0-500 mM NaCl gradient, as indicated by the straight line.
Figure 7:
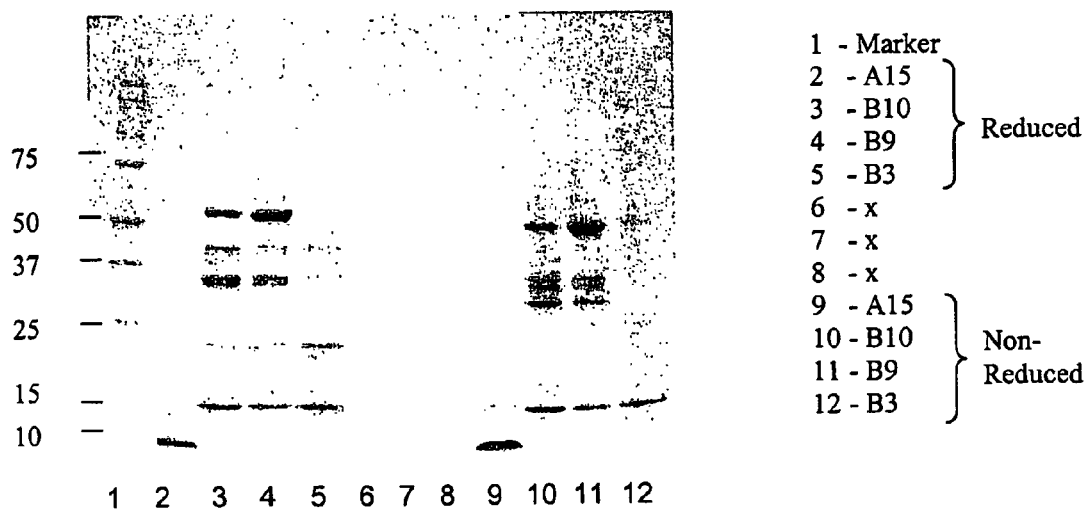
FIG. 7 shows the results of both reducing SDS-PAGE (Coomassie-stained) and non-reducing SDS-PAGE (Coomassie-stained) gels of fractions A15, B10, B9 and B3 from the column run illustrated by FIG. 6. Fractions B9 and B10 clearly contain protein corresponding to the expected size of the scDiS A6 TCR.
Figure 8:
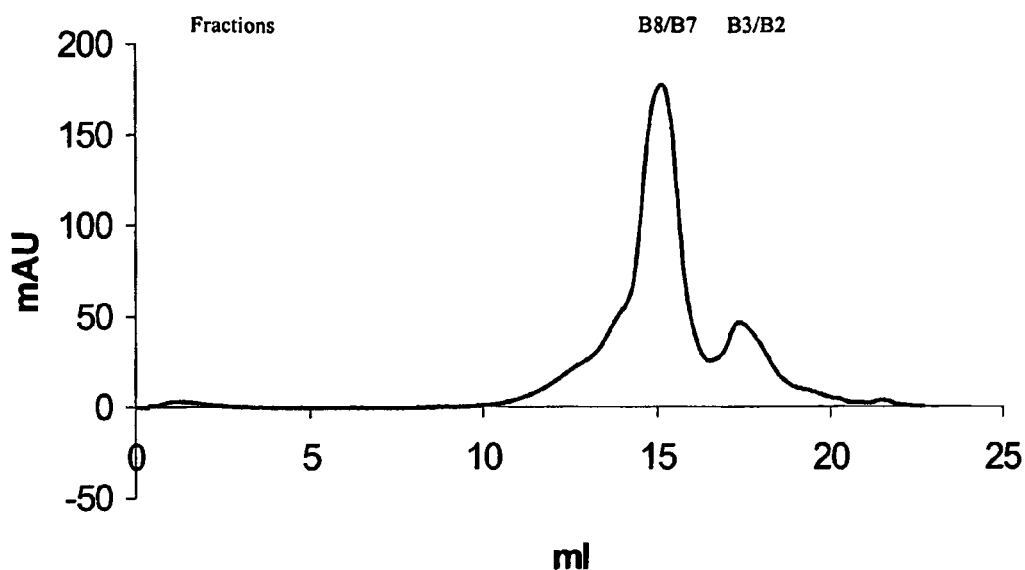
FIG. 8 illustrates the elution of the scDiS A6 TCR elution from a Superdex 200 gel filtration column of fractions B10-B7 from the ion exchange column run shown in FIG. 6.
Figure 9:
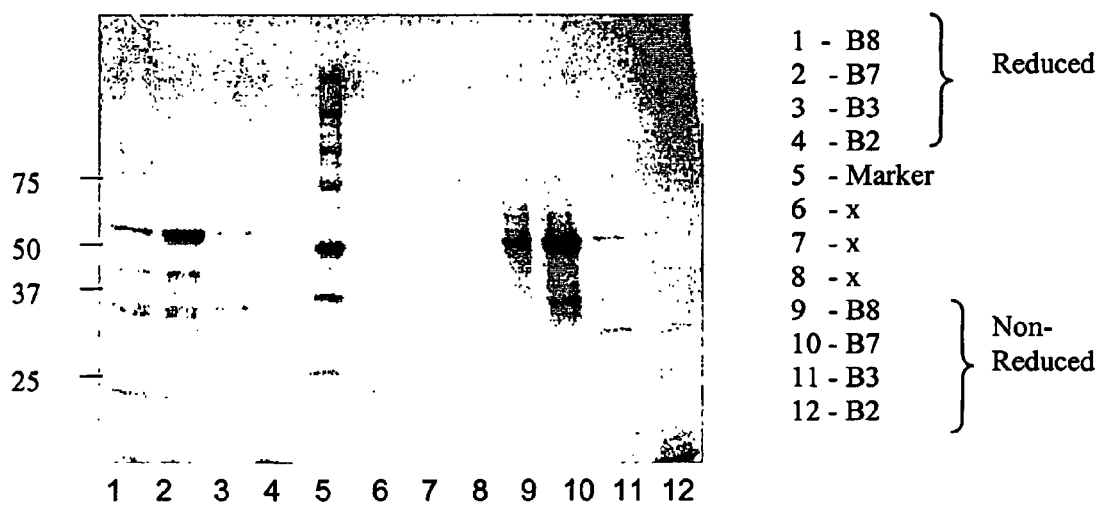
FIG. 9 shows the results of both reducing SDS-PAGE (Coomassie-stained) and non-reducing SDS-PAGE (Coomassie-stained) gels of fractions B8, B7, B3 and B2 from the gel filtration column run illustrated by FIG. 8. Fraction B7 clearly contains protein corresponding to the expected size of the scDiS A6 TCR.
Figure 10:
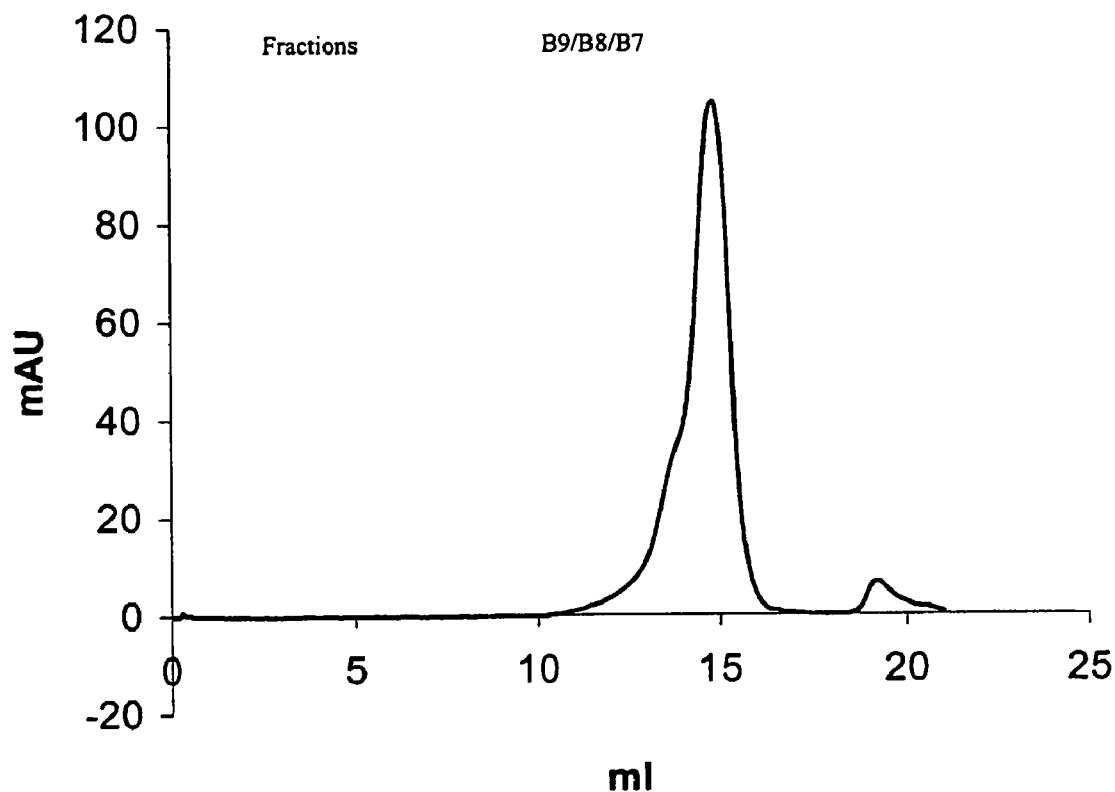
FIG. 10 is a final gel filtration run into BIAcore buffer of the concentrated fractions B9-B6 of the gel filtration run shown in FIG. 8. The scDiS A6 TCR elutes as a single major peak.
Figure 11:
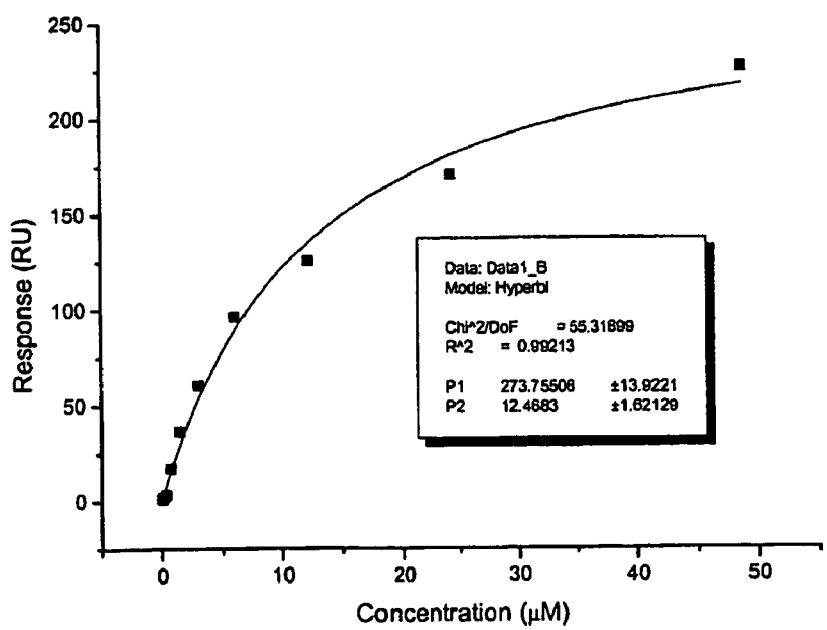
FIG. 11. BIAcore data for binding of the scDiS A6 TCR to HLA-A2 TAX.

Approximately 15 mg of the solubilised inclusion body chain was thawed from frozen stocks. The inclusion bodies were diluted to a final concentration of 5 mg/ml in 6M guanidine solution, and DTT (2M stock) was added to a final concentration of 10 mM. The mixture was incubated at 37° C. for 30 min. 1 liter of the following refolding buffer: 100 mM Tris pH 8.5, 400 mM L-Arginine, 2 mM EDTA, 5 mM reduced Glutathione, 0.5 mM oxidised Glutathione, 5M urea, 0.2 mM PMSF was prepared and stirred vigoursly at 5° C.±3° C. The redox couple (2-mercaptoethylamine and cystamine (to final concentrations of 6.6 mM and 3.7 mM, respectively) were added approximately 5 minutes before addition of the denatured TCR chains. The protein was then allowed to refold for approximately 5 hours±15 minutes with stirring at 5° C. ±3° C. The refold was then dialysed twice, firstly against 10 liters of 100 mM urea, secondly against 10 liters of 100 mM urea, 10 mM Tris pH 8.0. Both refolding and dialysis steps were carried out at 6-8° C.

scTCR was separated from degradation products and impurities by loading the dialysed refold onto a POROS 50HQ anion exchange column and eluting bound protein with a gradient of 0-500 mM NaCI over 50 column volumes using an Akta purifier (Pharmacia) as in FIG. 6. Peak fractions were stored at 4° C. and analysed by Coomassie-stained SDS-PAGE (FIG. 7) before being pooled and concentrated. The sTCR was then purified and characterised using a Superdex 200HR gel filtration column (FIG. 8) pre-equilibrated in HBS-EP buffer (10 mM HEPES pH 7.4, 150 mM NaCl, 3.5 mM EDTA, 0.05% nonidet p40). Peak fractions were stored at 4° C. and analysed by Coomassie-stained SDS-PAGE (FIG. 9) before being pooled and concentrated. Finally, concentrated fractions B9-B6 were run put through another gel filtration step in order to produce purified protein in BIAcore buffer, (FIG. 10) The peak eluting at a relative molecular weight of approximately 50 kDa was pooled. This was concentrated prior to characterisation by BIAcore surface plasmon resonance analysis.

Example 3

BIAcore Surface Plasmon Resonance Characterisation of scTCR Binding to HLA-A2 Tax A surface plasmon resonance biosensor (BIAcore 3000™) was used to analyse the binding of the A6 scTCR to its peptide-MHC ligand (HLA-A2 Tax). This was facilitated by producing single pMHC complexes (described below) which were immobilised to a streptavidin-coated binding surface in a semi-oriented fashion, allowing efficient testing of the binding of a soluble T-cell receptor to up to four different pMHC (immobilised on separate flow cells) simultaneously. Manual injection of HLA complex allows the precise level of immobilised class I molecules to be manipulated easily.

Such immobilised complexes are capable of binding both T-cell receptors and the coreceptor CD8αα, both of which may be injected in the soluble phase.

Biotinylated class I HLA-A2—Tax complexes were refolded in vitro from bacterially-expressed inclusion bodies containing the constituent subunit proteins and synthetic peptide, followed by purification and in vitro enzymatic biotinylation (O'Callaghan et al. (1999) *Anal. Biochem.* 266: 9-15). HLA-heavy chain was expressed with a C-terminal biotinylation tag which replaces the transmembrane and cytoplasmic domains of the protein in an appropriate construct. The HLA light-chain or β2-microglobulin was also expressed as inclusion bodies in *E. coli* from an appropriate construct, at a level of ~500 mg/liter bacterial culture.

*E. coli* cells were lysed and inclusion bodies are purified to approximately 80% purity. Protein from inclusion bodies was denatured in 6 M guanidine-HCl, 50 mM Tris pH 8.1, 100 mM NaCl, 10 mM DTT, 10 mM EDTA, and was refolded at a concentration of 30 mg/liter heavy chain, 30 mg/liter β2m into 0.4 M L-Arginine-HCl, 100 mM Tris pH 8.1, 3.7 mM cystamine, mM cysteamine, 4 mg/ml peptide (e.g. tax 11-19), by addition of a single pulse of denatured protein into refold buffer at <5° C. Refolding was allowed to reach completion at 4° C. for at least 1 hour.

Buffer was exchanged by dialysis in 10 volumes of 10 mM Tris pH 8.1. Two changes of buffer were necessary to reduce the ionic strength of the solution sufficiently. The protein solution was then filtered through a 1.5 µm cellulose acetate filter and loaded onto a POROS 50HQ anion exchange column (8 ml bed volume). Protein was eluted with a linear 0-500 mM NaCl gradient. HLA-A2-peptide complex eluted at approximately 250 mM NaCl, and peak fractions were collected, a cocktail of protease inhibitors (Calbiochem) was added and the fractions were chilled on ice.

Biotinylation tagged HLA complexes were buffer exchanged into 10 mM Tris pH 8.1, 5 mM NaCl using a Pharmacia fast desalting column equilibrated in the same buffer. Immediately upon elution, the protein-containing fractions were chilled on ice and protease inhibitor cocktail (Calbiochem) was added. Biotinylation reagents were then added: 1 mM biotin, 5 mM ATP (buffered to pH 8), 7.5 mM $MgCl_2$, and 5 µg/ml BirA enzyme (purified according to O'Callaghan et al. (1999) *Anal. Biochem.* 266: 9-15). The mixture was then allowed to incubate at room temperature overnight.

Biotinylated HLA complexes were purified using gel filtration chromatography. A Pharmacia Superdex 75 HR 10/30 column was pre-equilibrated with filtered PBS and 1 ml of the biotinylation reaction mixture was loaded and the column was developed with PBS at 0.5 ml/min. Biotinylated HLA complexes eluted as a single peak at approximately 15 ml. Fractions containing protein were pooled, chilled on ice, and protease inhibitor cocktail was added. Protein concentration was determined using a Coomassie-binding assay (PerBio) and aliquots of biotinylated HLA complexes were stored frozen at −20° C. Streptavidin was immobilised by standard amine coupling methods.

The interactions between A6 Tax scTCR containing a novel inter-chain bond and its ligand/MHC complex or an irrelevant HLA-peptide combination, the production of which is described above, were analysed on a BIAcore 3000™ surface plasmon resonance (SPR) biosensor. SPR measures changes in refractive index expressed in response units (RU) near a sensor surface within a small flow cell, a principle that can be used to detect receptor ligand interactions and to analyse their affinity and kinetic parameters. The probe flow cells were prepared by immobilising the individual HLA-peptide complexes in separate flow cells via binding between the biotin cross linked onto β2m and streptavidin which have been chemically cross linked to the activated surface of the flow cells. The assay was then performed by passing scTCR over the surfaces of the different flow cells at a constant flow rate, measuring the SPR response in doing so. Injections of soluble sTCR at constant flow rate and different concentrations over the peptide-HLA complex were used to define the background resonance. The values of these control measurements were subtracted from the values obtained with specific peptide-HLA complex and used to calculate binding affinities expressed as the dissociation constant, Kd (Price & Dwek, Principles and Problems in Physical Chemistry for Biochemists ($2^{nd}$ Edition) 1979, Clarendon Press, Oxford).

The BIAcore analysis of the scDiS A6 TCR demonstrated that this molecule bound specifically to its cognate ligand (HLA-A2 TAX) with a kd of 12.4±1.62 μM.

The invention claimed is:

1. A single chain T cell receptor (scTCR) comprising:
    an α segment constituted by a human TCR α chain variable region sequence fused to the N terminus of a human TCR α chain constant region extracellular sequence,
    a β segment constituted by a human TCR β chain variable region sequence fused to the N terminus of a human TCR β chain constant region extracellular sequence, and
    a linker sequence linking the C terminus of the α segment to the N terminus of the β segment, or vice versa,
    the constant region extracellular sequences of the α and β segments being linked by a disulfide bond,
the length of the linker sequence and the position of the disulfide bond being such that the variable region sequences of the α and β segments are mutually orientated substantially as in native αβ T cell receptors, wherein the scTCR is selected from the group consisting of:
    (a) a scTCR wherein the constant region extracellular sequence of the α segment includes a sequence corresponding to TRAC*01 and the β segment includes a sequence corresponding to TRBC1*01 or TRBC2*01, and a non-native disulfide bond is between cysteine residues substituted for Thr 48 of exon 1 of TRAC*01 (amino acid residue 10 of SEQ ID NO:2) and Ser 57 of exon 1 of TRBC1*01 or TRBC2*01 (amino acid residue 10 of SEQ ID NO:6);
    (b) a scTCR wherein a disulfide bond links cysteine residues substituted for Thr 45 of exon 1 of TRAC*01 (amino acid residue 10 of SEQ ID NO:3) and Ser 77 of exon 1 of TRBC1*01 or TRBC2*01 (amino acid residue 10 of SEQ ID NO:7);
    (c) a scTCR wherein a disulfide bond links cysteine residues substituted for Tyr 10 of exon 1 of TRAC*01 (amino acid residue 10 of SEQ ID NO:4) and Ser 17 of exon 1 of TRBC1*01 or TRBC2*01 (amino acid residue 10 of SEQ ID NO:8);
    (d) a scTCR wherein a disulfide bond links cysteine residues substituted for Thr 45 of exon 1 of TRAC*01 (amino acid residue 10 of SEQ ID NO:3) and Asp 59 of exon 1 of TRBC1*01 or TRBC2*01 (amino acid residue 10 of SEQ ID NO:9); and
    (e) a scTCR wherein a disulfide bond links cysteine residues substituted for Ser 15 of exon 1 of TRAC*01 (amino acid residue 10 of SEQ ID NO:5) and Glu 15 of exon 1 of TRBC1*01 or TRBC2*01 (amino acid residue 10 of SEQ ID NO:10).

2. A scTCR as claimed in claim 1 wherein the constant region extracellular sequence present in the α segment includes a sequence corresponding to the extracellular constant Ig domain of a TCR α chain, and/or the constant region extracellular sequence present in the β segments includes a sequence corresponding to the extracellular constant Ig domain of a TCR β chain.

3. A scTCR as claimed in claim 1 wherein the constant region extracellular sequences present in the α and β segments correspond to the constant regions of the α and β chains of a native TCR truncated at their C termini such that the cysteine residues which form the native interchain disulfide bond of the TCR are excluded.

4. A scTCR as claimed in claim 1 wherein the constant region extracellular sequences present in the α and β segments correspond to the constant regions of the α and β chains of a native TCR in which cysteine residues which form the native interchain disulfide bond are substituted by another amino acid residue.

5. A scTCR as claimed in claim 4, wherein the said cysteine residues are substituted by serine or alanine.

6. A scTCR as claimed in claim 1 wherein the linker sequence has the formula -P-AA-P- wherein P is proline and AA represents an amino acid sequence wherein the amino acids are glycine and serine.

7. A scTCR as claimed in claim 1 wherein the linker sequence links the C terminus of the α domain to the N terminus of the β domain.

8. A scTCR as claimed in claim 7 wherein the linker sequence consists of from 26 to 41 amino acids.

9. A scTCR as claimed in claim 7 wherein the linker sequence consists of 29, 30, 31 or 32 amino acids.

10. A scTCR as claimed in claim 7 wherein the linker sequence consists of 33, 34, 35 or 36 amino acids.

11. A scTCR as claimed in claim 7 wherein the linker sequence is -PGGG-(SGGGG)$_5$-P- (SEQ ID NO:1) wherein P is proline, G is glycine and S is serine.

12. A scTCR as claimed in claim 7 wherein the linker sequence is -PGGG-(SGGGG)$_6$-P- (SEQ ID NO:34) wherein P is proline, G is glycine and S is serine.

13. A sTCR as claimed in claim 1 in which an unpaired cysteine residue present in native TCR β chain is not present.

14. A scTCR as claimed in claim 1, wherein the constant region extracellular sequence of the α segment includes a sequence corresponding to TRAC*01 and the β segment includes a sequence corresponding to TRBC1*01 or TRBC2*01, and a non-native disulfide bond is between cysteine residues substituted for Thr 48 of exon 1 of TRAC*01 (amino acid residue 10 of SEQ ID NO:2) and Ser 57 of exon 1 of TRBC1*01 or TRBC2*01 (amino acid residue 10 of SEQ ID NO:6).

15. A scTCR as claimed in claim 1, wherein a disulfide bond links cysteine residues substituted for Thr 45 of exon 1 of TRAC*01 (amino acid residue 10 of SEQ ID NO:3) and Ser 77 of exon 1 of TRBC1*01 or TRBC2*01 (amino acid residue 10 of SEQ ID NO:7).

16. A scTCR as claimed in claim 1, wherein a disulfide bond links cysteine residues substituted for Tyr 10 of exon 1 of TRAC*01 (amino acid residue 10 of SEQ ID NO:4) and Ser 17 of exon 1 of TRBC1*01 or TRBC2*01 (amino acid residue 10 of SEQ ID NO:8).

17. A scTCR as claimed in claim 1, wherein a disulfide bond links cysteine residues substituted for Thr 45 of exon 1 of TRAC*01 (amino acid residue 10 of SEQ ID NO:3) and Asp 59 of exon 1 of TRBC1*01 or TRBC2*01 (amino acid residue 10 of SEQ ID NO:9).

18. A scTCR as claimed in claim 1, wherein a disulfide bond links cysteine residues substituted for Ser 15 of exon 1 of TRAC*01 (amino acid residue 10 of SEQ ID NO:5) and Glu 15 of exon 1 of TRBC1*01 or TRBC2*01 (amino acid residue 10 of SEQ ID NO:10).

19. A scTCR as claimed in claim 1 wherein the TCR is one which binds a peptide MHC complex.

20. A scTCR as claimed in claim 1 wherein the TCR is one which binds a superantigen or a peptide-MHC/superantigen complex.

21. A multivalent T cell receptor (TCR) complex comprising a plurality of sTCRs as claimed in claim 1.

22. A scTCR as claimed in claim 1 which is covalently linked to a therapeutic agent.

23. A scTCR as claimed in claim 1, or a plurality thereof, attached to a particle or bead.

24. A composition comprising a scTCR as claimed in claim 1 and a pharmaceutically acceptable carrier.

25. A method for detecting a TCR ligand selected from MHC-peptide complexes, CD1-antigen complexes, superantigens and MHC-peptide/superantigen complexes which comprises: providing a scTCR as claimed in claim 1, or a plurality thereof; contacting the scTCR with the TCR ligand; and detecting binding of the scTCR to the ligand.

26. A method of identifying an inhibitor of the interaction between a scTCR as claimed in claim 1, or a plurality thereof, and a TCR ligand selected from MHC-peptide complexes, CD 1-antigen complexes, superantigens and MHC-peptide/superantigen complexes comprising contacting the scTCR with a scTCR ligand, in the presence of and in the absence of a test compound, and determining whether the presence of the test compound reduces binding of the scTCR to the TCR ligand, such reduction being taken as identifying an inhibitor.

27. A method of identifying a potential inhibitor of the interaction between a scTCR as claimed in claim 1, or a plurality thereof, and a TCR ligand selected from MHC-peptide complexes, CD 1-antigen complexes, superantigens and MHC-peptide/superantigen complexes comprising contacting the scTCR with a test compound and determining whether the test compound binds to the scTCR, such binding being taken as identifying a potential inhibitor.

* * * * *

SEQUENCE LISTING

```
<160> NUMBER OF SEQ ID NOS: 41

<210> SEQ ID NO 1
<211> LENGTH: 30
<212> TYPE: PRT
<213> ORGANISM: Artificial sequence
<220> FEATURE:
<223> OTHER INFORMATION: scTCR Linker

<400> SEQUENCE: 1

Pro Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Pro
            20                  25                  30

<210> SEQ ID NO 2
<211> LENGTH: 20
<212> TYPE: PRT
<213> ORGANISM: Homo sapiens

<400> SEQUENCE: 2

Asp Ser Asp Val Tyr Ile Thr Asp Lys Thr Val Leu Asp Met Arg Ser
1               5                   10                  15

Met Asp Phe Lys
            20

<210> SEQ ID NO 3
<211> LENGTH: 20
<212> TYPE: PRT
<213> ORGANISM: Homo sapiens

<400> SEQUENCE: 3

Gln Ser Lys Asp Ser Asp Val Tyr Ile Thr Asp Lys Thr Val Leu Asp
1               5                   10                  15

Met Arg Ser Met
            20

<210> SEQ ID NO 4
<211> LENGTH: 20
<212> TYPE: PRT
<213> ORGANISM: Homo sapiens
```

-continued

```
<400> SEQUENCE: 4

Asp Ile Gln Asn Pro Asp Pro Ala Val Tyr Gln Leu Arg Asp Ser Lys
1               5                   10                  15

Ser Ser Asp Lys
            20

<210> SEQ ID NO 5
<211> LENGTH: 20
<212> TYPE: PRT
<213> ORGANISM: Homo sapiens

<400> SEQUENCE: 5

Asp Pro Ala Val Tyr Gln Leu Arg Asp Ser Lys Ser Ser Asp Lys Ser
1               5                   10                  15

Val Cys Leu Phe
            20

<210> SEQ ID NO 6
<211> LENGTH: 20
<212> TYPE: PRT
<213> ORGANISM: Homo sapiens

<400> SEQUENCE: 6

Asn Gly Lys Glu Val His Ser Gly Val Ser Thr Asp Pro Gln Pro Leu
1               5                   10                  15

Lys Glu Gln Pro
            20

<210> SEQ ID NO 7
<211> LENGTH: 20
<212> TYPE: PRT
<213> ORGANISM: Homo sapiens

<400> SEQUENCE: 7

Ala Leu Asn Asp Ser Arg Tyr Ala Leu Ser Ser Arg Leu Arg Val Ser
1               5                   10                  15

Ala Thr Phe Trp
            20

<210> SEQ ID NO 8
<211> LENGTH: 20
<212> TYPE: PRT
<213> ORGANISM: Homo sapiens

<400> SEQUENCE: 8

Pro Pro Glu Val Ala Val Phe Glu Pro Ser Glu Ala Glu Ile Ser His
1               5                   10                  15

Thr Gln Lys Ala
            20

<210> SEQ ID NO 9
<211> LENGTH: 20
<212> TYPE: PRT
<213> ORGANISM: Homo sapiens

<400> SEQUENCE: 9

Lys Glu Val His Ser Gly Val Ser Thr Asp Pro Gln Pro Leu Lys Glu
1               5                   10                  15

Gln Pro Ala Leu
            20
```

```
<210> SEQ ID NO 10
<211> LENGTH: 20
<212> TYPE: PRT
<213> ORGANISM: Homo sapiens

<400> SEQUENCE: 10

Val Phe Pro Pro Glu Val Ala Val Phe Glu Pro Ser Glu Ala Glu Ile
1               5                   10                  15

Ser His Thr Gln
            20

<210> SEQ ID NO 11
<211> LENGTH: 91
<212> TYPE: PRT
<213> ORGANISM: Mus musculus

<400> SEQUENCE: 11

Pro Tyr Ile Gln Asn Pro Glu Pro Ala Val Tyr Gln Leu Lys Asp Pro
1               5                   10                  15

Arg Ser Gln Asp Ser Thr Leu Cys Leu Phe Thr Asp Phe Asp Ser Gln
            20                  25                  30

Ile Asn Val Pro Lys Thr Met Glu Ser Gly Thr Phe Ile Thr Asp Lys
        35                  40                  45

Thr Val Leu Asp Met Lys Ala Met Asp Ser Lys Ser Asn Gly Ala Ile
50                  55                  60

Ala Trp Ser Asn Gln Thr Ser Phe Thr Cys Gln Asp Ile Phe Lys Glu
65                  70                  75                  80

Thr Asn Ala Thr Tyr Pro Ser Ser Asp Val Pro
                85                  90

<210> SEQ ID NO 12
<211> LENGTH: 126
<212> TYPE: PRT
<213> ORGANISM: Mus musculus

<400> SEQUENCE: 12

Glu Asp Leu Arg Asn Val Thr Pro Pro Lys Val Ser Leu Phe Glu Pro
1               5                   10                  15

Ser Lys Ala Glu Ile Ala Asn Lys Gln Lys Ala Thr Leu Val Cys Leu
            20                  25                  30

Ala Arg Gly Phe Phe Pro Asp His Val Glu Leu Ser Trp Trp Val Asn
        35                  40                  45

Gly Arg Glu Val His Ser Gly Val Ser Thr Asp Pro Gln Ala Tyr Lys
50                  55                  60

Glu Ser Asn Tyr Ser Tyr Cys Leu Ser Ser Arg Leu Arg Val Ser Ala
65                  70                  75                  80

Thr Phe Trp His Asn Pro Arg Asn His Phe Arg Cys Gln Val Gln Phe
                85                  90                  95

His Gly Leu Ser Glu Glu Asp Lys Trp Pro Glu Gly Ser Pro Lys Pro
            100                 105                 110

Val Thr Gln Asn Ile Ser Ala Glu Ala Trp Gly Arg Ala Asp
            115                 120                 125

<210> SEQ ID NO 13
<211> LENGTH: 20
<212> TYPE: PRT
<213> ORGANISM: Mus musculus
```

-continued

```
<400> SEQUENCE: 13

Glu Ser Gly Thr Phe Ile Thr Asp Lys Thr Val Leu Asp Met Lys Ala
1               5                   10                  15

Met Asp Ser Lys
            20

<210> SEQ ID NO 14
<211> LENGTH: 20
<212> TYPE: PRT
<213> ORGANISM: Mus musculus

<400> SEQUENCE: 14

Lys Thr Met Glu Ser Gly Thr Phe Ile Thr Asp Lys Thr Val Leu Asp
1               5                   10                  15

Met Lys Ala Met
            20

<210> SEQ ID NO 15
<211> LENGTH: 20
<212> TYPE: PRT
<213> ORGANISM: Mus musculus

<400> SEQUENCE: 15

Tyr Ile Gln Asn Pro Glu Pro Ala Val Tyr Gln Leu Lys Asp Pro Arg
1               5                   10                  15

Ser Gln Asp Ser
            20

<210> SEQ ID NO 16
<211> LENGTH: 20
<212> TYPE: PRT
<213> ORGANISM: Mus musculus

<400> SEQUENCE: 16

Ala Val Tyr Gln Leu Lys Asp Pro Arg Ser Gln Asp Ser Thr Leu Cys
1               5                   10                  15

Leu Phe Thr Asp
            20

<210> SEQ ID NO 17
<211> LENGTH: 20
<212> TYPE: PRT
<213> ORGANISM: Mus musculus

<400> SEQUENCE: 17

Asn Gly Arg Glu Val His Ser Gly Val Ser Thr Asp Pro Gln Ala Tyr
1               5                   10                  15

Lys Glu Ser Asn
            20

<210> SEQ ID NO 18
<211> LENGTH: 20
<212> TYPE: PRT
<213> ORGANISM: Mus musculus

<400> SEQUENCE: 18

Lys Glu Ser Asn Tyr Ser Tyr Cys Leu Ser Ser Arg Leu Arg Val Ser
1               5                   10                  15

Ala Thr Phe Trp
            20
```

```
<210> SEQ ID NO 19
<211> LENGTH: 20
<212> TYPE: PRT
<213> ORGANISM: Mus musculus

<400> SEQUENCE: 19

Pro Pro Lys Val Ser Leu Phe Glu Pro Ser Lys Ala Glu Ile Ala Asn
1               5                   10                  15

Lys Gln Lys Ala
            20

<210> SEQ ID NO 20
<211> LENGTH: 20
<212> TYPE: PRT
<213> ORGANISM: Mus musculus

<400> SEQUENCE: 20

Arg Glu Val His Ser Gly Val Ser Thr Asp Pro Gln Ala Tyr Lys Glu
1               5                   10                  15

Ser Asn Tyr Ser
            20

<210> SEQ ID NO 21
<211> LENGTH: 20
<212> TYPE: PRT
<213> ORGANISM: Mus musculus

<400> SEQUENCE: 21

Val Thr Pro Pro Lys Val Ser Leu Phe Glu Pro Ser Lys Ala Glu Ile
1               5                   10                  15

Ala Asn Lys Gln
            20

<210> SEQ ID NO 22
<211> LENGTH: 24
<212> TYPE: DNA
<213> ORGANISM: Artificial sequence
<220> FEATURE:
<223> OTHER INFORMATION: Primer

<400> SEQUENCE: 22
cacagacaaa tgtgtgctag acat                                          24

<210> SEQ ID NO 23
<211> LENGTH: 24
<212> TYPE: DNA
<213> ORGANISM: Artificial sequence
<220> FEATURE:
<223> OTHER INFORMATION: Primer

<400> SEQUENCE: 23
atgtctagca cacatttgtc tgtg                                          24

<210> SEQ ID NO 24
<211> LENGTH: 21
<212> TYPE: DNA
<213> ORGANISM: Artificial sequence
<220> FEATURE:
<223> OTHER INFORMATION: Primer

<400> SEQUENCE: 24
cagtggggtc tgcacagacc c                                             21
```

<210> SEQ ID NO 25
<211> LENGTH: 21
<212> TYPE: DNA
<213> ORGANISM: Artificial sequence
<220> FEATURE:
<223> OTHER INFORMATION: Primer

<400> SEQUENCE: 25
gggtctgtgc agaccccact g                                            21

<210> SEQ ID NO 26
<211> LENGTH: 37
<212> TYPE: DNA
<213> ORGANISM: Artificial sequence
<220> FEATURE:
<223> OTHER INFORMATION: Primer

<400> SEQUENCE: 26
ccaaggccat atgcagaagg aagtggagca gaactct                           37

<210> SEQ ID NO 27
<211> LENGTH: 45
<212> TYPE: DNA
<213> ORGANISM: Artificial sequence
<220> FEATURE:
<223> OTHER INFORMATION: Primer

<400> SEQUENCE: 27
ttgggcccgc cggatccgcc cccgggggaa ctttctgggc tgggg                  45

<210> SEQ ID NO 28
<211> LENGTH: 45
<212> TYPE: DNA
<213> ORGANISM: Artificial sequence
<220> FEATURE:
<223> OTHER INFORMATION: Primer

<400> SEQUENCE: 28
tcccccgggg gcggatccgg cgggcccaac gctggtgtca ctcag                  45

<210> SEQ ID NO 29
<211> LENGTH: 32
<212> TYPE: DNA
<213> ORGANISM: Artificial sequence
<220> FEATURE:
<223> OTHER INFORMATION: Primer

<400> SEQUENCE: 29
gggaagctta gtctgctcta ccccaggcct cg                                32

<210> SEQ ID NO 30
<211> LENGTH: 39
<212> TYPE: DNA
<213> ORGANISM: Artificial sequence
<220> FEATURE:
<223> OTHER INFORMATION: Primer

<400> SEQUENCE: 30 ccggggggtgg ctctggcggt ggcggttcag gcggtggcg                        39

<210> SEQ ID NO 31
<211> LENGTH: 39
<212> TYPE: DNA
<213> ORGANISM: Artificial sequence
<220> FEATURE:
<223> OTHER INFORMATION: Primer

<400> SEQUENCE: 31
gatccgccac cgcctgaacc gccaccgcca gagccaccc                          39

<210> SEQ ID NO 32
<211> LENGTH: 37
<212> TYPE: DNA
<213> ORGANISM: Artificial sequence
<220> FEATURE:
<223> OTHER INFORMATION: Primer

<400> SEQUENCE: 32
gcggatccgg cggtggcggt tcgggtggcg gtggctc                            37

<210> SEQ ID NO 33
<211> LENGTH: 38
<212> TYPE: DNA
<213> ORGANISM: Artificial sequence
<220> FEATURE:
<223> OTHER INFORMATION: Primer

<400> SEQUENCE: 33
gtgggcccgc caccgcctga gccaccgcca cccgaacc                           38

<210> SEQ ID NO 34
<211> LENGTH: 35
<212> TYPE: PRT
<213> ORGANISM: Artificial sequence
<220> FEATURE:
<223> OTHER INFORMATION: scTCR Linker

<400> SEQUENCE: 34

Pro Gly Gly Gly Ser Gly Gly Gly Ser Gly Gly Gly Ser Gly
1               5                   10                  15

Gly Gly Ser Gly Gly Gly Ser Gly Gly Gly Ser Gly Gly
            20                  25                  30

Gly Gly Pro
        35

<210> SEQ ID NO 35
<211> LENGTH: 621
<212> TYPE: DNA
<213> ORGANISM: Homo sapiens

<400> SEQUENCE: 35
atgcagaagg aagtggagca gaactctgga cccctcagtg ttccagaggg agccattgcc    60
tctctcaact gcacttacag tgaccgaggt tcccagtcct tcttctggta cagacaatat   120
tctgggaaaa gccctgagtt gataatgtcc atatactcca atggtgacaa agaagatgga   180
aggtttacag cacagctcaa taagccagc cagtatgttt ctctgctcat cagagactcc   240
cagcccagtg attcagccac ctacctctgt gccgttacaa ctgacagctg ggggaaattg   300
cagtttggag cagggaccca ggttgtggtc accccagata ccagaaccc tgaccctgcc   360 gtgtaccagc tgagagactc taaatccagt gacaagtctg tctgcctatt caccgatttt   420
gattctcaaa caaatgtgtc acaaagtaag gattctgatg tgtatatcac agacaaatgt   480
gtgctagaca tgaggtctat ggacttcaag agcaacagtg ctgtggcctg gagcaacaaa   540
tctgactttg catgtgcaaa cgccttcaac aacagcatta ttccagaaga caccttcttc   600
cccagcccag aaagttccta a                                             621

<210> SEQ ID NO 36
<211> LENGTH: 741
<212> TYPE: DNA
<213> ORGANISM: Homo sapiens

<400> SEQUENCE: 36

```
atgaacgctg gtgtcactca gaccccaaaa ttccaggtcc tgaagacagg acagagcatg      60
acactgcagt gtgcccagga tatgaaccat gaatacatgt cctggtatcg acaagaccca     120
ggcatggggc tgaggctgat tcattactca gttggtgctg gtatcactga ccaaggagaa     180
gtccccaatg ctacaatgt ctccagatca accacagagg atttcccgct caggctgctg     240
tcggctgctc cctcccagac atctgtgtac ttctgtgcca gcaggccggg actagcggga     300
gggcgaccag agcagtactt cgggccgggc accaggctca cggtcacaga ggacctgaaa     360
aacgtgttcc cacccgaggt cgctgtgttt gagccatcag aagcagagat ctcccacacc     420
caaaaggcca cactggtgtg cctggccaca ggcttctacc ccgaccacgt ggagctgagc     480
tggtgggtga atgggaagga ggtgcacagt ggggtctgca cagacccgca gcccctcaag     540
gagcagcccg ccctcaatga ctccagatac gctctgagca gccgcctgag ggtctcggcc     600
accttctggc aggacccccg caaccacttc cgctgtcaag tccagttcta cgggctctcg     660
gagaatgacg agtggaccca ggatagggcc aaacccgtca cccagatcgt cagcgccgag     720
gcctggggta gagcagacta a                                               741
```

<210> SEQ ID NO 37
<211> LENGTH: 206
<212> TYPE: PRT
<213> ORGANISM: Homo sapiens

<400> SEQUENCE: 37

```
Met Gln Lys Glu Val Glu Gln Asn Ser Gly Pro Leu Ser Val Pro Glu
1               5                   10                  15

Gly Ala Ile Ala Ser Leu Asn Cys Thr Tyr Ser Asp Arg Gly Ser Gln
                20                  25                  30

Ser Phe Phe Trp Tyr Arg Gln Tyr Ser Gly Lys Ser Pro Glu Leu Ile
            35                  40                  45

Met Ser Ile Tyr Ser Asn Gly Asp Lys Glu Asp Gly Arg Phe Thr Ala
        50                  55                  60

Gln Leu Asn Lys Ala Ser Gln Tyr Val Ser Leu Leu Ile Arg Asp Ser
65                  70                  75                  80

Gln Pro Ser Asp Ser Ala Thr Tyr Leu Cys Ala Val Thr Thr Asp Ser
                85                  90                  95

Trp Gly Lys Leu Gln Phe Gly Ala Gly Thr Gln Val Val Val Thr Pro
            100                 105                 110

Asp Ile Gln Asn Pro Asp Pro Ala Val Tyr Gln Leu Arg Asp Ser Lys
        115                 120                 125

Ser Ser Asp Lys Ser Val Cys Leu Phe Thr Asp Phe Asp Ser Gln Thr
    130                 135                 140

Asn Val Ser Gln Ser Lys Asp Ser Asp Val Tyr Ile Thr Asp Lys Cys
145                 150                 155                 160

Val Leu Asp Met Arg Ser Met Asp Phe Lys Ser Asn Ser Ala Val Ala
                165                 170                 175

Trp Ser Asn Lys Ser Asp Phe Ala Cys Ala Asn Ala Phe Asn Asn Ser
            180                 185                 190

Ile Ile Pro Glu Asp Thr Phe Phe Pro Ser Pro Glu Ser Ser
        195                 200                 205
```

<210> SEQ ID NO 38
<211> LENGTH: 246
<212> TYPE: PRT
<213> ORGANISM: Homo sapiens

<400> SEQUENCE: 38

```
Met Asn Ala Gly Val Thr Gln Thr Pro Lys Phe Gln Val Leu Lys Thr
1               5                   10                  15
Gly Gln Ser Met Thr Leu Gln Cys Ala Gln Asp Met Asn His Glu Tyr
            20                  25                  30
Met Ser Trp Tyr Arg Gln Asp Pro Gly Met Gly Leu Arg Leu Ile His
        35                  40                  45
Tyr Ser Val Gly Ala Gly Ile Thr Asp Gln Gly Glu Val Pro Asn Gly
    50                  55                  60
Tyr Asn Val Ser Arg Ser Thr Thr Glu Asp Phe Pro Leu Arg Leu Leu
65                  70                  75                  80
Ser Ala Ala Pro Ser Gln Thr Ser Val Tyr Phe Cys Ala Ser Arg Pro
                85                  90                  95
Gly Leu Ala Gly Gly Arg Pro Glu Gln Tyr Phe Gly Pro Gly Thr Arg
            100                 105                 110
Leu Thr Val Thr Glu Asp Leu Lys Asn Val Phe Pro Pro Glu Val Ala
        115                 120                 125
Val Phe Glu Pro Ser Glu Ala Glu Ile Ser His Thr Gln Lys Ala Thr
    130                 135                 140
Leu Val Cys Leu Ala Thr Gly Phe Tyr Pro Asp His Val Glu Leu Ser
145                 150                 155                 160
Trp Trp Val Asn Gly Lys Glu Val His Ser Gly Val Cys Thr Asp Pro
                165                 170                 175
Gln Pro Leu Lys Glu Gln Pro Ala Leu Asn Asp Ser Arg Tyr Ala Leu
            180                 185                 190
Ser Ser Arg Leu Arg Val Ser Ala Thr Phe Trp Gln Asp Pro Arg Asn
        195                 200                 205
His Phe Arg Cys Gln Val Gln Phe Tyr Gly Leu Ser Glu Asn Asp Glu
    210                 215                 220
Trp Thr Gln Asp Arg Ala Lys Pro Val Thr Gln Ile Val Ser Ala Glu
225                 230                 235                 240
Ala Trp Gly Arg Ala Asp
                245
```

<210> SEQ ID NO 39
<211> LENGTH: 90
<212> TYPE: DNA
<213> ORGANISM: Artificial Sequence
<220> FEATURE:
<223> OTHER INFORMATION: DNA encoding scTCR linker

<400> SEQUENCE: 39

```
cccgggggtg gctctggcgg tggcggttca ggcggtggcg gatccggcgg tggcggttcg    60
ggtggcggtg gctcaggcgg tggcgggccc                                    90
```

<210> SEQ ID NO 40
<211> LENGTH: 1446
<212> TYPE: DNA
<213> ORGANISM: Artificial sequence
<220> FEATURE:
<223> OTHER INFORMATION: sc DiS TCR

```
<400> SEQUENCE: 40
atgcagaagg aagtggagca gaactctgga cccctcagtg ttccagaggg agccattgcc      60
tctctcaact gcacttacag tgaccgaggt tcccagtcct tcttctggta cagacaatat    120
tctgggaaaa gccctgagtt gataatgtcc atatactcca atggtgacaa agaagatgga    180
aggtttacag cacagctcaa taaagccagc cagtatgttt ctctgctcat cagagactcc    240
cagcccagtg attcagccac ctacctctgt gccgttacaa ctgacagctg ggggaaattg    300
cagtttggag cagggaccca ggttgtggtc accccagata tccagaaccc tgaccctgcc    360
gtgtaccagc tgagagactc taaatccagt gacaagtctg tctgcctatt caccgatttt    420
gattctcaaa caaatgtgtc acaaagtaag gattctgatg tgtatatcac agacaaatgt    480
gtgctagaca tgaggtctat ggacttcaag agcaacagtg ctgtggcctg agcaacaaa    540 tctgactttg catgtgcaaa cgccttcaac aacagcatta ttccagaaga caccttcttc    600
cccagcccag aaagttcccc cgggggtggc tctggcggtg gcggttcagg cggtggcgga    660
tccggcggtg gcggttcggg tggcggtggc tcaggcggtg gcgggcccaa cgctggtgtc    720
actcagaccc caaaattcca ggtcctgaag acaggacaga gcatgacact gcagtgtgcc    780
caggatatga accatgaata catgtcctgg tatcgacaag acccaggcat ggggctgagg    840
ctgattcatt actcagttgg tgctggtatc actgaccaag agaagtccc caatggctac    900 aatgtctcca gatcaaccac agaggatttc ccgctcaggc tgctgtcggc tgctccctcc    960
cagacatctg tgtacttctg tgccagcagg ccgggactag cggagggcg accagagcag   1020 tacttcgggc cgggcaccag gctcacggtc acagaggacc tgaaaaacgt gttcccaccc   1080
gaggtcgctg tgtttgagcc atcagaagca gagatctccc acacccaaaa ggccacactg   1140
gtgtgcctgg ccacaggctt ctaccccgac cacgtggagc tgagctggtg ggtgaatggg   1200
aaggaggtgc acagtggggt ctgcacagac ccgcagcccc tcaaggagca gcccgccctc   1260
aatgactcca gatacgctct gagcagccgc ctgagggtct cggccacctt ctggcaggac   1320
ccccgcaacc acttccgctg tcaagtccag ttctacgggc tctcggagaa tgacgagtgg   1380
acccaggata gggccaaacc cgtcacccag atcgtcagcg ccgaggcctg ggtagagca   1440 gactaa                                                              1446

<210> SEQ ID NO 41
<211> LENGTH: 481
<212> TYPE: PRT
<213> ORGANISM: Artificial sequence
<220> FEATURE:
<223> OTHER INFORMATION: sc DiS TCR

<400> SEQUENCE: 41

Met Gln Lys Glu Val Glu Gln Asn Ser Gly Pro Leu Ser Val Pro Glu
 1               5                  10                  15

Gly Ala Ile Ala Ser Leu Asn Cys Thr Tyr Ser Asp Arg Gly Ser Gln
                20                  25                  30

Ser Phe Phe Trp Tyr Arg Gln Tyr Ser Gly Lys Ser Pro Glu Leu Ile
            35                  40                  45

Met Ser Ile Tyr Ser Asn Gly Asp Lys Glu Asp Gly Arg Phe Thr Ala
        50                  55                  60

Gln Leu Asn Lys Ala Ser Gln Tyr Val Ser Leu Leu Ile Arg Asp Ser
 65                 70                  75                  80

Gln Pro Ser Asp Ser Ala Thr Tyr Leu Cys Ala Val Thr Thr Asp Ser
                85                  90                  95
```

-continued

```
Trp Gly Lys Leu Gln Phe Gly Ala Gly Thr Gln Val Val Thr Pro
            100                 105                 110
Asp Ile Gln Asn Pro Asp Pro Ala Val Tyr Gln Leu Arg Asp Ser Lys
            115                 120                 125
Ser Ser Asp Lys Ser Val Cys Leu Phe Thr Asp Phe Asp Ser Gln Thr
            130                 135                 140
Asn Val Ser Gln Ser Lys Asp Ser Asp Val Tyr Ile Thr Asp Lys Cys
145                 150                 155                 160
Val Leu Asp Met Arg Ser Met Asp Phe Lys Ser Asn Ser Ala Val Ala
                165                 170                 175
Trp Ser Asn Lys Ser Asp Phe Ala Cys Ala Asn Ala Phe Asn Asn Ser
                180                 185                 190
Ile Ile Pro Glu Asp Thr Phe Phe Pro Ser Pro Glu Ser Ser Pro Gly
                195                 200                 205
Gly Gly Ser Gly Gly Gly Ser Gly Gly Gly Ser Gly Gly Gly
            210                 215                 220
Gly Ser Gly Gly Gly Ser Gly Gly Gly Pro Asn Ala Gly Val
225                 230                 235                 240
Thr Gln Thr Pro Lys Phe Gln Val Leu Lys Thr Gly Gln Ser Met Thr
                245                 250                 255
Leu Gln Cys Ala Gln Asp Met Asn His Glu Tyr Met Ser Trp Tyr Arg
                260                 265                 270
Gln Asp Pro Gly Met Gly Leu Arg Leu Ile His Tyr Ser Val Gly Ala
                275                 280                 285
Gly Ile Thr Asp Gln Gly Glu Val Pro Asn Gly Tyr Asn Val Ser Arg
            290                 295                 300
Ser Thr Thr Glu Asp Phe Pro Leu Arg Leu Leu Ser Ala Ala Pro Ser
305                 310                 315                 320
Gln Thr Ser Val Tyr Phe Cys Ala Ser Arg Pro Gly Leu Ala Gly Gly
                325                 330                 335
Arg Pro Glu Gln Tyr Phe Gly Pro Gly Thr Arg Leu Thr Val Thr Glu
                340                 345                 350
Asp Leu Lys Asn Val Phe Pro Pro Glu Val Ala Val Phe Glu Pro Ser
                355                 360                 365
Glu Ala Glu Ile Ser His Thr Gln Lys Ala Thr Leu Val Cys Leu Ala
            370                 375                 380
Thr Gly Phe Tyr Pro Asp His Val Glu Leu Ser Trp Trp Val Asn Gly
385                 390                 395                 400
Lys Glu Val His Ser Gly Val Cys Thr Asp Pro Gln Pro Leu Lys Glu
                405                 410                 415
Gln Pro Ala Leu Asn Asp Ser Arg Tyr Ala Leu Ser Ser Arg Leu Arg
                420                 425                 430
Val Ser Ala Thr Phe Trp Gln Asp Pro Arg Asn His Phe Arg Cys Gln
                435                 440                 445
Val Gln Phe Tyr Gly Leu Ser Glu Asn Asp Glu Trp Thr Gln Asp Arg
            450                 455                 460
Ala Lys Pro Val Thr Gln Ile Val Ser Ala Glu Ala Trp Gly Arg Ala
465                 470                 475                 480
Asp
```